(12) United States Patent
Okada et al.

(10) Patent No.: US 9,266,905 B2
(45) Date of Patent: Feb. 23, 2016

(54) COLOR MATERIAL AND METHOD FOR PRODUCING THE SAME

(75) Inventors: Masato Okada, Tokyo-to (JP); Satoshi Kinoshita, Osaka (JP)

(73) Assignees: DAI NIPPON PRINTING CO., LTD., Tokyo-to (JP); YAMAMOTO CHEMICALS, INC., Yao-shi, Osaka (JP)

(*) Notice: Subject to any disclaimer, the term of this patent is extended or adjusted under 35 U.S.C. 154(b) by 79 days.

(21) Appl. No.: 14/112,283

(22) PCT Filed: Apr. 18, 2012

(86) PCT No.: PCT/JP2012/060462
§ 371 (c)(1),
(2), (4) Date: Oct. 17, 2013

(87) PCT Pub. No.: WO2012/144520
PCT Pub. Date: Oct. 26, 2012

(65) Prior Publication Data
US 2014/0039201 A1   Feb. 6, 2014

(30) Foreign Application Priority Data

Apr. 21, 2011  (JP) ................................. 2011-095369
Aug. 15, 2011  (JP) ................................. 2011-177727
Apr. 16, 2012  (JP) ................................. 2012-093182

(51) Int. Cl.
| | |
|---|---|
| C07C 251/24 | (2006.01) |
| C09B 11/12 | (2006.01) |
| C07F 1/08 | (2006.01) |
| C09B 11/28 | (2006.01) |
| C07C 251/00 | (2006.01) |
| C07C 309/35 | (2006.01) |
| G03F 7/00 | (2006.01) |

(52) U.S. Cl.
CPC ................. *C07F 1/08* (2013.01); *C07C 251/00* (2013.01); *C07C 309/35* (2013.01); *C09B 11/12* (2013.01); *C09B 11/28* (2013.01); *G03F 7/0007* (2013.01)

(58) Field of Classification Search
None
See application file for complete search history.

(56) References Cited

U.S. PATENT DOCUMENTS

| | | |
|---|---|---|
| 4,223,144 A | 9/1980 | Kast et al. |
| 5,051,504 A | 9/1991 | Hahn et al. |
| 9,005,722 B2 * | 4/2015 | Okada .......................... 428/1.31 |
| 2010/0192312 A1 | 8/2010 | Cremer et al. |
| 2011/0049444 A1 | 3/2011 | Sako et al. |

FOREIGN PATENT DOCUMENTS

| | | |
|---|---|---|
| JP | 54-50030 A | 4/1979 |
| JP | 01269585 A | 10/1989 |
| JP | 03-024166 A | 2/1991 |
| JP | 2008304766 A | 12/2008 |
| JP | 2010526897 A | 8/2010 |
| JP | 2011007847 A | 1/2011 |
| JP | 2011213925 A | 10/2011 |
| JP | 2012007121 A | 1/2012 |
| JP | 2012032754 A | 2/2012 |
| WO | 2009/107734 A1 | 9/2009 |
| WO | 2011/122707 A1 | 10/2011 |
| WO | 2011/162217 A1 | 12/2011 |

OTHER PUBLICATIONS

U.S. Appl. No. 14/112,980, filed Oct. 2013, Okada, Masato.*
U.S. Appl. No. 14/396,217, filed Oct. 2014, Okada, Masato.*
International Search Report issued Dec. 18, 2012; PCT/JP2012/077003.

* cited by examiner

*Primary Examiner* — Michael Barker
(74) *Attorney, Agent, or Firm* — Ladas & Parry LLP

(57) ABSTRACT

Color materials represented by the following general formula (I):

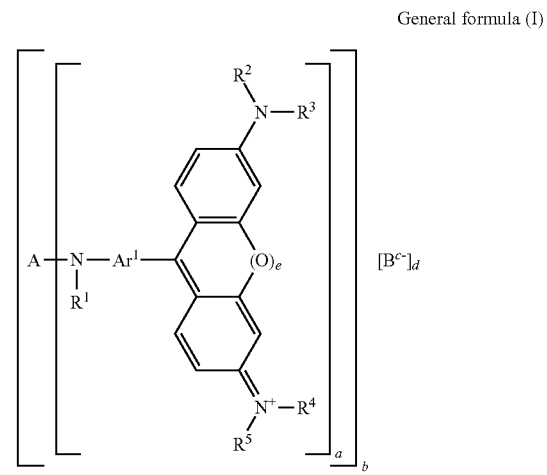

General formula (I)

having excellent heat resistance.

4 Claims, 1 Drawing Sheet

COLOR MATERIAL AND METHOD FOR PRODUCING THE SAME

TECHNICAL FIELD

The present invention relates to a novel color material with excellent heat resistance particularly, and a method for producing the same.

BACKGROUND ART

Nowadays, a large number of dyes are known, and they are largely categorized into natural dyes and synthetic dyes. Examples of the synthetic dyes include aniline blue, fuchsine and methyl orange. Most of the synthetic dyes have an aromatic or heterocyclic ring, and they are classified as either ionic compounds (for example, all water-soluble dyes) or non-ionic compounds (for example, disperse dyes). In addition, in the case of the ionic dyes, they are categorized into anionic (negative ionic) dyes and cationic (positive ionic) dyes.

The cationic dyes comprise an organic cation having a positive charge delocalized over a conjugated bond and normally an inorganic anion. Also, the cationic dyes are generally dyes in which an amino group which may have a substituent is involved in resonance. Therefore, selection of the cationic dyes depends on the number and kinds of the anion being a counter ion. Examples of the counter anion include a chloride ion, a bromide ion, an iodide ion, a perchlorate ion, a tetrafluoroborate ion, a hexafluorophosphate ion, an alkyl or aryl sulfate ion, a tosilate ion, an acetate ion and an oxalate ion.

Generally, rhodamine, safranine and victoria blue, which are cationic dyes, contain a chloride ion or tosilate ion as a counter ion. However, these compounds have insufficient heat resistance.

An example is known, in which a chloride ion or an aryl sulfate ion is used as a counter anion of a triarylmethane dye to improve heat durability of the triarylmethane dye (for example, Patent Literature 1).

In Patent Literature 2, as a method of obtaining a color composition for color filters with excellent color characteristics, heat resistance, light resistance and solvent resistance, a salt-forming compound comprising a triarylmethane basic dye and a sulfonated organic compound having at least two sulfonic groups, is disclosed.

In Patent Literature 3, as a method of obtaining a coloring resin composition which has not only excellent light resistance but also excellent light resistance, a salt forming method has been reported, in which a salt is formed by using a sulfonated compound of a dye skeleton such as phthalocyanine or anthraquinone, which is the counter anion, in combination with a triarylmethane skeleton, which is the cation.

However, the salt-forming compounds containing a dye and a counter anion disclosed in Patent Literatures to 3 are insufficient in heat resistance. Accordingly, there has been a desire for a color material with increased heat resistance.

A polysiloxane dye is disclosed in Patent Literature 4, which is highly cross-linked by polysiloxane containing at least ten Si atoms. Due to its synthesis method, the polysiloxane dye disclosed in Patent Literature 4 is a mixture in which an unreacted compound having only one dye skeleton or dyes with different polymerization degrees are present. It is difficult to separate only a dye with a specific polymerization degree from the polysiloxane dye, so that there is a problem with the productivity of the polysiloxane dye. Since the polysiloxane dye contains a silanol group or alkoxysilyl group, a siloxane bond is formed between the polysiloxane dye(s) or between the polysiloxane dye and other component having a silanol group or alkoxysilyl group. As a result, there is a deterioration in the state of a solution or dispersion liquid comprising the polysiloxane dye, such as a change in solubility or an influence on dispersion stability, thus making it difficult to handle the solution or dispersion liquid. Such a reaction is likely to proceed particularly upon heating, therefore it is not suitable to use the polysiloxane dye under heating at high temperature. As will be described in Comparative Examples hereinafter, the above-mentioned polysiloxane dye is insufficient in heat resistance.

CITATION LIST

Patent Literature

[Patent Literature 1] Japanese Patent Application Laid-Open (JP-A) No. 2008-304766
[Patent Literature 2] JP-A No. 2011-7847
[Patent Literature 3] WO2009/107734
[Patent Literature 4] Japanese translation of PCT International Application No. 2010-526897

SUMMARY OF INVENTION

Technical Problem

The present invention has been made in view of the above circumstances, and it is an object of the present invention to provide a color material with excellent heat resistance, and a method for producing the color material in high purity and high yield.

Solution to Problem

The color material of the present invention is a compound represented by the following general formula (I):

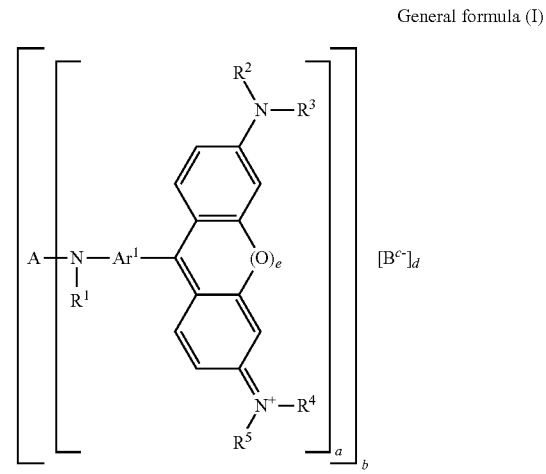

General formula (I)

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N may be contained in a carbon chain of the organic group; $B^{c-}$ is a "c"-valent anion; each of $R^1$ to $R^5$ is independently a hydrogen atom, an alkyl group which may have a substituent, or an aryl group which may have a substituent; $R^2$ and $R^3$ may be bound to form a ring structure, and/or $R^4$ and $R^5$ may be bound to form a ring structure; $Ar^1$ is a divalent aromatic group which may have a substituent; $R^1$s may be the same or different; $R^2$s may be the same or different; $R^3$s may be the same or different; $R^4$s may be the same or different; $R^5$s may be the same or different; and $Ar^1$s may be the same or different; and wherein each of "a" and "c" is an integer of 2 or more; each of "b" and "d" is an integer of 1 or more; "e" is 0 or 1 and there is no bond when "e" is 0; and "e"s may be the same or different.

In the color material of the present invention, from the viewpoint of heat resistance, it is preferable that the anion ($B^{c-}$) in the general formula (I) is an organic anion having a sulfonato group ($-SO_3^-$ group).

In the color material of the present invention, from the viewpoint of heat resistance, it is preferable that the anion ($B^{c-}$) in the general formula (I) is one or more anions selected from the group consisting of those represented by the following general formulae (II), (III) and (IV):

$$Ar^2 +\!\!-\!\!SO_3^-]_c \qquad \text{General formula (II)}$$

wherein $Ar^2$ is a "c"-valent aromatic group which may have a substituent, and "c" is an integer of 2 or more;

General formula (III)

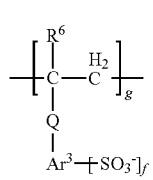

wherein $R^6$ is a hydrogen atom or a methyl group; $Ar^3$ is an aromatic group which may have a substituent; Q is a direct bond or a divalent linking group; "f" is an integer of 1 or more; and "g" is an integer of 2 or more; and General formula (IV)

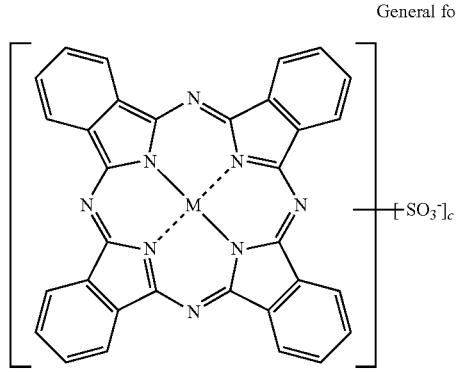

wherein M represents two hydrogen atoms or one selected from the group consisting of Cu, Mg, Al, Ni, Co, Fe and Zn; the sulfonato group ($-SO_3^-$ group) is bound to an aromatic ring by substitution; and "c" is an integer of 2 to 4.

In the color material of the present invention, from the viewpoint of heat resistance, it is preferable that the anion ($B^{c-}$) in the general formula (I) is an anion of an inorganic acid containing molybdenum and/or tungsten.

In the color material of the present invention, from the viewpoint of ease of production, it is preferable that "a" in the general formula (I) is 4 or less.

From the viewpoint of heat resistance, it is preferable that the color material of the present invention is a color material for being dispersed in a solvent having a solubility of the color material of 0.1 (mg/10 g solvent) or less at 23° C.

The method for producing the color material represented by the following general formula (I) of the present invention comprises the step of: performing a condensation reaction between a compound represented by the following general formula (A) and a compound represented by the following general formula (B):

General formula (A)

General formula (B)

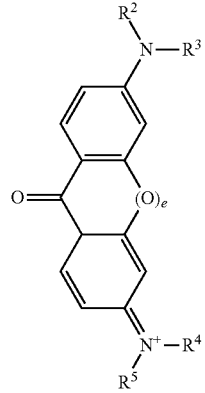

General formula (I)

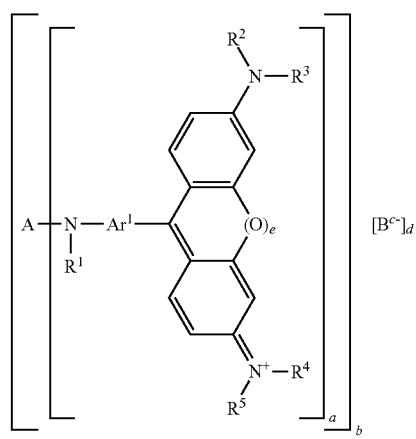

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N may be contained in a carbon chain of the organic group; $B^{c-}$ is a "c"-valent anion; each of $R^1$ to $R^5$ is independently a hydrogen atom, an alkyl group which may have a substituent, or an aryl group which may have a substituent; $R^2$ and $R^3$ may be bound to form a ring structure, and/or $R^4$ and $R^5$ may be bound to form a ring structure; $Ar^1$ is a divalent aromatic group which may have a substituent; $Ar^{1'}$ is a monovalent aromatic group in which a hydrogen atom is bound to $Ar^1$; $R^1$s may be the same or different; $R^2$s may be the same or different; $R^3$s may be the same or different; $R^4$s may be the same or different; $R^5$s may be the same or different; and $Ar^1$s may be the same or different; and wherein each of "a" and "c" is an integer of 2 or more; each of "b" and "d" is an integer of 1 or more; "e" is 0 or 1 and there is no bond when "e" is 0; and "e"s may be the same or different.

Advantageous Effects of Invention

The present invention provides a color material with excellent heat resistance, and a method for producing the color material in high purity and high yield.

DESCRIPTION OF EMBODIMENTS

Hereinafter, the present invention will be described in detail.
The color material of the present invention is a compound represented by the following general formula (I):

General formula (I)

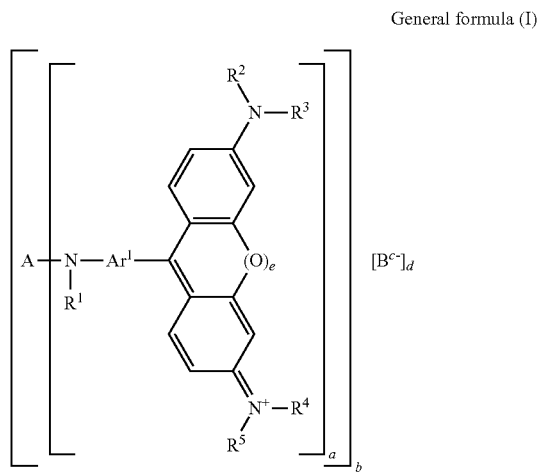

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N may be contained in a carbon chain of the organic group; $B^{c-}$ is a "c"-valent anion; each of $R^1$ to $R^5$ is independently a hydrogen atom, an alkyl group which may have a substituent, or an aryl group which may have a substituent; $R^2$ and $R^3$ may be bound to form a ring structure, and/or $R^4$ and $R^5$ may be bound to form a ring structure; $Ar^1$ is a divalent aromatic group which may have a substituent; $R^1$s may be the same or different; $R^2$s may be the same or different; $R^3$s may be the same or different; $R^4$s may be the same or different; $R^5$s may be the same or different; and $Ar^1$s may be the same or different; and wherein each of "a" and "c" is an integer of 2 or more; each of "b" and "d" is an integer of 1 or more; "e" is 0 or 1 and there is no bond when "e" is 0; and "e"s may be the same or different.

The color material of the present invention is excellent in heat resistance, particularly. The mechanism of production of these effects by the above-specified combination is not understood yet; however, it is estimated as follows.

Figure 2:
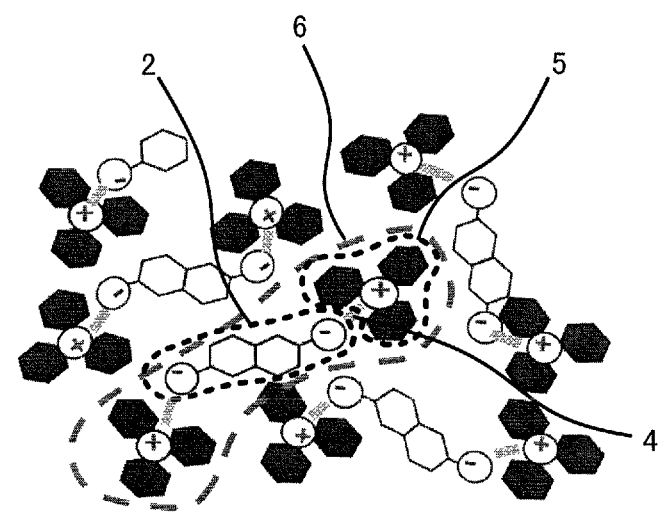
FIG. 2 is a schematical view showing ionic bonds of a conventional dye salt-forming compound.

Conventionally, there has been a problem that dyes have generally low heat resistance. As a means for overcoming this problem, there has been employed a method of making dyes into a salt-forming compound. For example, as a method of forming a salt with a triarylmethane dye, there is a method using a divalent anion as a counter anion (for example, Patent Literature 2). According to this method, as shown in FIG. 2, a divalent counter anion 2 can form ionic bonds with two dye cations 5, thereby heat resistance is increased compared with the case using only a dye. However, even by employing such a method, sufficient heat resistance cannot be obtained.

Figure 1:
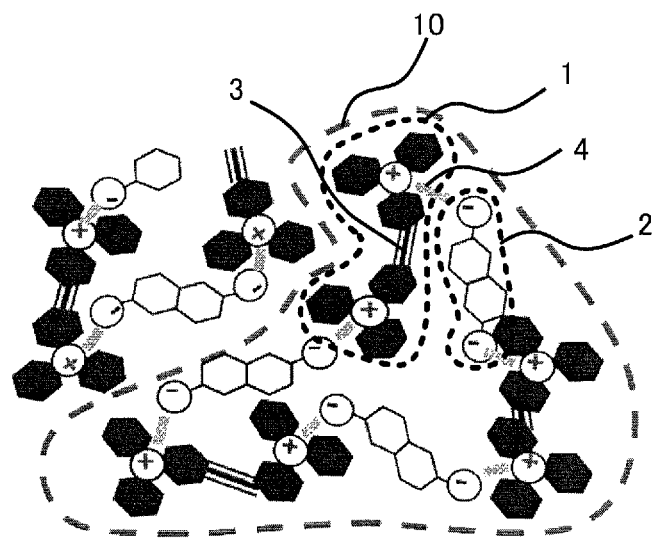
FIG. 1 is a schematical view showing a molecular association state of the color material of the present invention.

As shown in FIG. 1, as well as divalent or higher counter anions 2, the color material represented by the general formula (I) of the present invention has divalent or higher counter cations 1, in which two or more cationic color-forming moieties are bound through linkage 3 by A. For example, in the case where both anions and cations are divalent ions, it is assumed that in the aggregate of the color material, each of the anions and each of the cations do not merely form an ionic bond on a one molecule-to-one molecule (one-to-one) basis, but a molecular association 10 is formed, in which plural molecules are continuously connected through ionic bonds and associated, as shown in FIG. 1. The molecular association 10 behaves like one molecule in the aggregate of the color material, so that the apparent molecular weight of the molecular association is significantly more than the molecular weight of the conventional salt-forming compound. In addition, the formation of the molecular association 10 makes the cohesion in a solid state higher, thus decreasing the motion by heat and increasing the electric stability. Therefore, it is assumed that the dissociation of the ion pairs and the decomposition of the cationic moieties can be inhibited, which results in improved heat resistance.

In the color material represented by the general formula (I), among the hydrocarbons of linking group A, the hydrocarbon that is directly bound to the cationic color-forming moiety has no π bond; therefore, there is almost no change in the color characteristics of the cationic color-forming moiety such as color tone and transmittance, before and after the introduction of the linking group A.

Hereinafter, the color material represented by the general formula (I) will be described.

The cationic moiety of the color material used in the present invention is a divalent or higher cation having a structure represented by the following general formula (V). Unlike the conventional triarylmethane basic dyes and xanthene basic dyes, even a chloride of the cationic moiety represented by the following general formula (V) does not substantially dissolve in water.

The structure represented by the following general formula (V) refers to a divalent or higher cation, in which cations each containing only one conventional triarylmethane skeleton are bound through "a"-valent covalent bonds.

If it is considered that the binding species connecting a monocation consisting of only one conventional triarylmethane skeleton and an anion is an ionic bond only, it can be considered that the binding species of the salt-forming component consisting of the divalent or higher cation of the present invention includes covalent bonds which connect monocations in addition to ionic bonds. Therefore, it is assumed that since the salt-forming component comprising the divalent or higher cation having the structure represented by the following general formula (V) contains an increased amount of stronger binding species throughout the constituent elements compared to the conventional salt-forming component comprising one triarylmethane skeleton only, there is an increase in the stability of the salt-forming component and the component hardly cause hydration. Furthermore, it is assumed that since the molecular weight and hydrophobicity of the structure represented by the following general formula (V) are increased due to the linking group A, the divalent or higher cation becomes substantially insoluble in water, in cooperation with an increase in the stability of bonds.

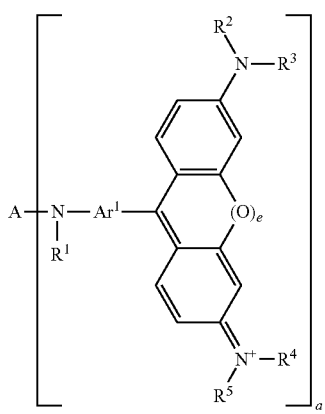

General formula (V)

In this formula, A, $R^1$ to $R^5$, $Ar^1$, "a" and "e" are the same as those in the general formula (I).

In the general formula (I), "e" is an integer of 0 or 1. When "e" is 0, the present invention has the triarylmethane skeleton represented by the following general formula (VI):

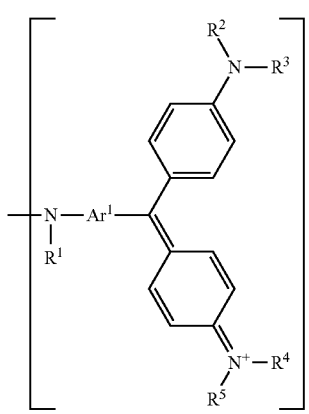

General formula (VI)

wherein $R^1$ to $R^5$ and $Ar^1$ are the same as those in the general formula (I).

When "e" is 1, the present invention has a xanthene skeleton represented by the following general formula (VII):

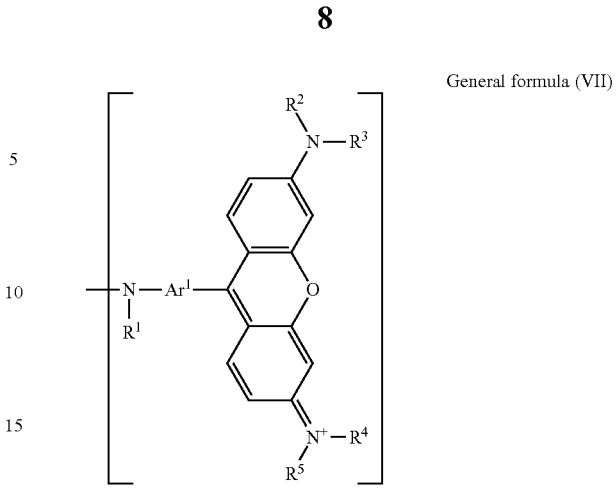

General formula (VII)

wherein $R^1$ to $R^5$ and $Ar^1$ are the same as those in the general formula (I).

In the general formula (I), "e"s may be the same or different. The examples include a cationic moiety having a plurality of triarylmethane or xanthene skeletons only, and a cationic moiety having both triarylmethane and xanthene skeletons per molecule. From the viewpoint of color purity, the cationic moiety having the same skeletons only is preferable. On the other hand, by having the cationic moiety including both triarylmethane and xanthene skeletons, or depending on the combination of the substituents that will be described hereinafter, it is possible to adjust the color of the color material represented by the general formula (I) to a desired color.

In the general formula (I), A is an "a"-valent organic group in which a carbon atom directly bound to N (nitrogen atom) has no π bond. The organic group is an aliphatic hydrocarbon group having a saturated aliphatic hydrocarbon group at least at a terminal position directly bound to N, or an aromatic group having the aliphatic hydrocarbon group, and O (oxygen atom), S (sulfur atom), N (nitrogen atom) may be contained in a carbon chain of the organic group. Since the carbon atom directly bound to N has no π bond, the color characteristics of the cationic color-forming moieties such as color tone and transmittance, are not affected by the linking group A and other color-forming moieties, thereby allowing the same color as that of a single color-forming moiety.

In A, as long as the carbon atom being at the terminal position and directly bound to N has no π bond, the aliphatic hydrocarbon group having a saturated aliphatic hydrocarbon group at least at a terminal position directly bound to N, may be in a linear, branched or cyclic form, have an unsaturated bond in carbon atoms except the one in the terminal position, have a substituent, or contain O, S, N in the carbon chain. For example, a carbonyl group, a carboxyl group, an oxycarbonyl group and/or an amide group may be contained, a hydrogen atom may be substituted with a halogen atom, etc.

Also in A, as the aromatic group having an aliphatic hydrocarbon group, there may be exemplified a monocyclic or polycyclic aromatic group which has an aliphatic hydrocarbon group having a saturated aliphatic hydrocarbon group at least at the terminal position directly bound to N. The aromatic group may have a substituent, and it may be a heterocyclic ring containing O, S or N.

Particularly, from the viewpoint of skeleton toughness, it is preferable that A contains a cyclic aliphatic hydrocarbon group or an aromatic group.

As the cyclic aliphatic hydrocarbon group, a bridged alicyclic hydrocarbon group is particularly preferable from the viewpoint of skeleton toughness. The bridged alicyclic hydrocarbon group refers to a polycyclic aliphatic hydrocarbon group having a bridged structure in the aliphatic ring and having a polycyclic structure. The examples include norbornane, bicyclo[2,2,2]octane and adamantane. Of bridged alicyclic hydrocarbon groups, norbornane is preferable. Examples of the aromatic group include groups containing a benzene ring and those containing a naphthalene ring. Of them, groups containing a benzene ring are preferable.

From the viewpoint of availability of raw materials, "A" is preferably divalent. When A is a divalent organic group, examples of the divalent organic group include a linear, branched or cyclic alkylene group having 1 to 20 carbon atoms, and an aromatic group in which two alkylene groups each having 1 to 20 carbon atoms are bound by substitution, such as a xylylene group.

The alkyl group at each of $R^1$ to $R^5$ is not particularly limited. Examples of the alkyl group include a linear or branched alkyl group having 1 to 20 carbon atoms. Of them, preferred is a linear or branched alkyl group having 1 to 8 carbon atoms, more preferred is a linear or branched alkyl group having 1 to 5 carbon atoms, from the viewpoint of ease of production and availability of raw materials. Of them, still more preferred is an ethyl group or a methyl group. A substituent that the alkyl group may have is not particularly limited. The examples include an aryl group, a halogen atom and a hydroxyl group. As the substituted alkyl group, a benzyl group can be exemplified.

The aryl group at each of $R^1$ to $R^5$ is not particularly limited. The examples include a phenyl group and a naphthyl group. As a substituent that the aryl group may have, an alkyl group and a halogen atom can be exemplified.

"$R^2$ and $R^3$ may be bound to form a ring structure, and/or $R^4$ and $R^5$ may be bound to form a ring structure" means that $R^2$ and $R^3$ form a ring structure through a nitrogen atom and/or $R^4$ and $R^5$ form a ring structure through a nitrogen atom. The ring structure is not particularly limited, and the examples include a pyrrolidine ring, a piperidine ring and a morpholine ring.

Particularly, from the viewpoint of chemical stability, it is preferable that each of $R^1$ to $R^5$ is independently a hydrogen atom, an alkyl group having 1 to 5 carbon atoms or a phenyl group. Or, it is preferable that $R^2$ and $R^3$ are bound to form a pyrrolidine ring, a piperidine ring or a morpholine ring, and/or $R^4$ and $R^5$ are bound to form a pyrrolidine ring, a piperidine ring or a morpholine ring.

Each of $R^1$ to $R^5$ independently may have the above structure. Particularly, from the viewpoint of color purity, it is preferable that $R^1$ is a hydrogen atom. From the viewpoint of easiness in production and availability of raw materials, it is more preferable that all of $R^2$ to $R^5$ are the same.

The divalent aromatic group in $Ar^1$ is not particularly limited. The aromatic group may be a heterocyclic group or an aromatic hydrocarbon group composed of a carbon ring. Examples of the aromatic hydrocarbon in the aromatic hydrocarbon group include: a benzene ring; condensed polycyclic aromatic hydrocarbons such as a naphthalene ring, a tetralin ring, an indene ring, a fluorene ring, an anthracene ring and a phenanthrene ring; and chain polycyclic hydrocarbon groups such as biphenyl, terphenyl, diphenylmethane, triphenylmethane and stilbene. The chain polycyclic hydrocarbon may have a hetero atom such as O and S in a chain skeleton, such as diphenyl ether. On the other hand, examples of the heterocyclic ring in the heterocyclic group include: five-membered heterocyclic rings such as furan, thiophene, pyrrol, oxazole, thiazole, imidazole and pyrazole; six-membered heterocyclic rings such as pyran, pyrone, pyridine, pyrone, pyridazine, pyrimidine and pyrazine; and condensed polycyclic heterocyclic rings such as benzofuran, thionaphthene, indole, carbazole, coumalin, benzo-pyrone, quinoline, isoquinoline, acridine, phthalazine, quinazoline and quinoxaline. These aromatic groups may have a substituent.

As the substituent that the aromatic group may have, an alkyl group having 1 to 5 carbon atoms and a halogen atom can be exemplified.

$Ar^1$ is preferably an aromatic group having 6 to 20 carbon atoms, more preferably an aromatic group having a condensed polycyclic carbon ring having 10 to 14 carbon atoms. Still more preferred are a phenylene group and a naphthylene group, from the point of view that the structure is simple and the raw materials are low-cost.

$R^1$s per molecule may be the same or different; $R^2$s per molecule may be the same or different; $R^3$s per molecule may be the same or different; $R^4$s per molecule may be the same or different; $R^5$s per molecule may be the same or different; and $Ar^1$s per molecule may be the same or different. The color-forming moieties can exhibit the same color when, in all of the moieties, $R^1$s are the same; $R^2$s are the same; $R^3$s are the same; $R^4$s are the same; $R^5$s are the same; and $Ar^1$s are the same. In this case, therefore, the color material can reproduce the same color as that of a single color-forming moiety, which is preferable from the viewpoint of color purity. On the other hand, if at least one selected from the group consisting of $R^1$s, $R^2$s, $R^3$s, $R^4$s, $R^5$s and $Ar^1$s is changed to a different substituent, it is possible to reproduce a color obtained from a mixture of several kinds of color-forming moieties, so that it is possible to produce a desired color.

In the color material of the present invention, the anionic moiety is a divalent or higher anion having the structure represented by ($B^{c-}$). $B^{c-}$ is not particularly limited as long as it is a divalent or higher anion, and it may be an organic anion or an inorganic anion. Herein, "organic anion" means an anion containing at least one carbon atom. "Inorganic anion" means an anion containing no carbon atom.

In the case that $B^{c-}$ is an organic anion, the structure is not particularly limited. However, it is particularly preferable that $B^{c-}$ is an organic group having an anionic substituent.

Examples of the anionic substituent include: imide acid groups such as $-SO_2N^-SO_2CH_3$, $-SO_2N^-COCH_3$, $-SO_2N^-SO_2CF_3$, $-SO_2N^-COCF_3$, $-CF_2SO_2N^-SO_2CH_3$, $-CF_2SO_2N^-COCH_3$, $-CF_2SO_2N^-SO_2CF_3$ and $-CF_2SO_2N^-COCF_3$; and substituents such as $-SO_3^-$, $-CF_2SO_3^-$, $-PO_3^{2-}$, $-COO^-$, $-CF_2PO_3^{2-}$ and $-CF_2COO^-$.

Particularly, from the viewpoint of stabilizing the cation and the coloration of the color material, it is preferable to use two or more monovalent anionic substituents. In addition, from the viewpoint of availability of raw materials and production cost, and also from the point of view that it is highly effective in stabilizing the cation due to their high acidity and thus keeping the state of coloration, preferred are an imide acid group, $-SO_3^-$ and $-CF_2SO_3^-$, and more preferred is $-SO_3^-$ (sulfonato group).

In the case of introducing a plurality of anionic substituents by substitution, the same kind or different kinds of substituents may be used.

The organic group to which the anionic substituent is introduced is not particularly limited. Examples of the organic group include a linear, branched or cyclic saturated or unsaturated hydrocarbon group, monocyclic or polycyclic aromatic group and groups that are combinations thereof. In the carbon chain of these organic groups, hetero atoms such as O, S, N may be contained, a carbonyl group, a carboxyl group, an oxycarbonyl group and an amide group may be contained, and hydrogen atoms may be substituted. As a substituent that the organic group may have, for example, a halogen atom can be exemplified.

Examples of the organic group to which the anionic substituent is introduced include: hydrocarbons such as cyclopropane, cyclobutane, cyclopentane, cyclohexane, norbornane, bicyclo[2,2,2]hexane, bicyclo[3,2,3]octane and adamantine; and aromatic compounds such as benzene, naphthalene, anthracene, phenanthrene, pyrene, triphenylene, fluorene, furan, thiophene, pyrrol, imidazole, pyran, pyridine, pyrimidine, pyrazine, triazine, indole, purine, quinoline, isoquinoline, xanthene and carbazole. Furthermore, the organic group may have a substituent such as a halogen atom or an alkyl group.

Of the above, as the organic group to which the anionic substituent is introduced, preferred are a monocyclic or polycyclic aromatic hydrocarbon group and a group that is a combination thereof, from the point of view that it is easy to introduce the anionic substituent.

In the case of intending not to change color by anions, it is preferable to use an organic group having an absorption maximum in the wavelength range of 400 nm or less. Examples of such an organic group include: organic groups having a condensed polycyclic carbon ring, such as naphthalene, tetralin, indene, fluorene, anthracene and phenanthrene; organic groups having a chain polycyclic hydrocarbon, such as biphenyl, terphenyl, diphenylmethane, triphenylmethane and stilbene; organic groups having a five-membered heterocyclic ring, such as furan, thiophene, pyrrol, oxazole, thiazole, imidazole and pyrazole; aromatic compounds comprising a six-membered heterocyclic ring, such as pyran, pyrone, pyridine, pyridazine, pyrimidine or pyrazine; and organic groups comprising a condensed polycyclic heterocyclic ring, such as benzofuran, thionaphthene, indole, carbazole, coumalin, benzo-pyrone, quinoline, isoquinoline, acridine, phthalazine, quinazoline and quinoxaline.

As the organic group to which the anionic substituent is introduced, there may be used a skeleton derived from an azo dye, an anthraquinone dye, a triphenylmethane dye, a xanthene dye, a phthalocyanine dye or an indigo dye, each of which is an organic compound or an organic metal compound. Alternatively, a dye selected from conventionally-known acid dyes, direct dyes and acid mordant dyes may be used.

In the case of using the dye-derived skeleton, the acid dye, the direct dye or the acid mordant dye, the obtained color tone of the color material changes; therefore, it is possible to adjust the color tone of the color material represented by the general formula (I) to a desired color.

Examples of the acid dyes include: C. I. Acid Yellow 1, 3, 7, 9, 11, 17, 23, 25, 29, 34, 36, 38, 40, 42, 54, 65, 72, 73, 76, 79, 98, 99, 111, 112, 113, 114, 116, 119, 123, 128, 134, 135, 138, 139, 140, 144, 150, 155, 157, 160, 161, 163, 168, 169, 172, 177, 178, 179, 184, 190, 193, 196, 197, 199, 202, 203, 204, 205, 207, 212, 214, 220, 221, 228, 230, 232, 235, 238, 240, 242, 243 and 251; C. I. Acid Red 1, 4, 8, 14, 17, 18, 26, 27, 29, 31, 34, 35, 37, 42, 44, 50, 51, 52, 57, 66, 73, 80, 87, 88, 91, 92, 94, 97, 103, 111, 114, 129, 133, 134, 138, 143, 145, 150, 151, 158, 176, 182, 183, 198, 206, 211, 215, 216, 217, 227, 228, 249, 252, 257, 258, 260, 261, 266, 268, 270, 274, 277, 280, 281, 195, 308, 312, 315, 316, 339, 341, 345, 346, 349, 382, 383, 394, 401, 412, 417, 418, 422 and 426; C. I. Acid Orange 6, 7, 8, 10, 12, 26, 50, 51, 52, 56, 62, 63, 64, 74, 75, 94, 95, 107, 108, 169 and 173; C. I. Acid Blue 1, 7, 9, 15, 18, 23, 25, 27, 29, 40, 42, 45, 51, 62, 70, 74, 80, 83, 86, 87, 90, 92, 96, 103, 112, 113, 120, 129, 138, 147, 150, 158, 171, 182, 192, 210, 242, 243, 256, 259, 267, 278, 280, 285, 290, 296, 315, 324:1, 335 and 340; C. I. Acid Violet 6B, 7, 9, 17 and 19; and C. I. Acid Green 1, 3, 5, 9, 16, 25, 27, 50, 58, 63, 65, 80, 104, 105, 106 and 109.

Examples of the direct dyes include: C. I. Direct Yellow 2, 33, 34, 35, 38, 39, 43, 47, 50, 54, 58, 68, 69, 70, 71, 86, 93, 94, 95, 98, 102, 108, 109, 129, 136, 138 and 141; C. I. Direct Red 79, 82, 83, 84, 91, 92, 96, 97, 98, 99, 105, 106, 107, 172, 173, 176, 177, 179, 181, 182, 184, 204, 207, 211, 213, 218, 220, 221, 222, 232, 233, 234, 241, 243, 246 and 250; C. I. Direct Orange 34, 39, 41, 46, 50, 52, 56, 57, 61, 64, 65, 68, 70, 96, 97, 106 and 107; C. I. Direct Blue 57, 77, 80, 81, 84, 85, 86, 90, 93, 94, 95, 97, 98, 99, 100, 101, 106, 107, 108, 109, 113, 114, 115, 117, 119, 137, 149, 150, 153, 155, 156, 158, 159, 160, 161, 162, 163, 164, 166, 167, 170, 171, 172, 173, 188, 189, 190, 192, 193, 194, 196, 198, 199, 200, 207, 209, 210, 212, 213, 214, 222, 228, 229, 237, 238, 242, 243, 244, 245, 247, 248, 250, 251, 252, 256, 257, 259, 260, 268, 274, 275 and 293; C. I. Direct Violet 47, 52, 54, 59, 60, 65, 66, 79, 80, 81, 82, 84, 89, 90, 93, 95, 96, 103 and 104; and C. I. Direct Green 25, 27, 31, 32, 34, 37, 63, 65, 66, 67, 68, 69, 72, 77, 79 and 82.

Examples of the acid mordant dyes include: C. I. Mordant Yellow 5, 8, 10, 16, 20, 26, 30, 31, 33, 42, 43, 45, 56, 61, 62 and 65; C. I. Mordant Red 1, 2, 3, 4, 9, 11, 12, 14, 17, 18, 19, 22, 23, 24, 25, 26, 30, 32, 33, 36, 37, 38, 39, 41, 43, 45, 46, 48, 53, 56, 63, 71, 74, 85, 86, 88, 90, 94 and 95; C. I. Mordant Orange 3, 4, 5, 8, 12, 13, 14, 20, 21, 23, 24, 28, 29, 32, 34, 35, 36, 37, 42, 43, 47 and 48; C. I. Mordant Blue 1, 2, 3, 7, 8, 9, 12, 13, 15, 16, 19, 20, 21, 22, 23, 24, 26, 30, 31, 32, 39, 40, 41, 43, 44, 48, 49, 53, 61, 74, 77, 83 and 84; C. I. Mordant Violet 1, 2, 4, 5, 7, 14, 22, 24, 30, 31, 32, 37, 40, 41, 44, 45, 47, 48, 53 and 58; and C. I. Mordant Green 1, 3, 4, 5, 10, 15, 19, 26, 29, 33, 34, 35, 41, 43 and 53.

Of the dyes listed above, in the case of selecting a dye wherein the dye itself is a divalent or higher anion, the dye can be used as it is as the anionic moiety in the color material of the present invention. In the case of selecting a dye wherein the dye itself is not a divalent or higher anion, an anionic substituent is appropriately introduced into the dye so that the dye can be a divalent or higher anion.

In the color material of the present invention, from the viewpoint of improving heat resistance, the anion ($B^{e-}$) in the general formula (I) is preferably one or more anions selected from the group consisting of those represented by the following general formulae (II), (III) and (IV):

$$Ar^2\!+\!SO_3^-]_c \qquad \text{General formula (II)}$$

wherein $Ar^2$ is a "c"-valent aromatic group which may have a substituent, and "c" is an integer of 2 or more;

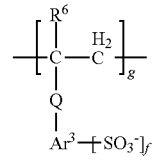

General formula (III)

wherein $R^6$ is a hydrogen atom or a methyl group; $Ar^3$ is an aromatic group which may have a substituent; Q is a direct bond or a divalent linking group; "f" is an integer of 1 or more; and "g" is an integer of 2 or more; and General formula (IV)

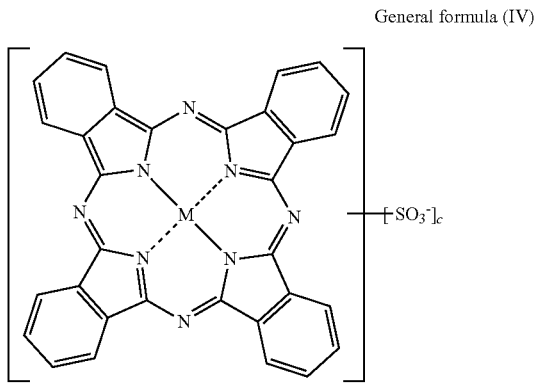

wherein M represents two hydrogen atoms or one selected from the group consisting of Cu, Mg, Al, N Co, Fe and Zn; a sulfonato group (—$SO_3^-$ group) is bound to an aromatic ring by substitution; and "c" is an integer of 2 to 4.

In the case of using the anion represented by the above general formula (II) as the anionic moiety of the color material of the present invention, since the color of the anion is colorless or pale yellow, the color material thus produced has a feature that it can keep the inherent color of the cation represented by the general formula (I).

In the case of using the anion represented by the general formula (III) as the anionic moiety of the color material of the present invention, there is an increase in the valence of anion and thus a possible interaction with more cations represented by the general formula (I). As the result, there is an increase in cohesion and insolubility in a solvent.

In the case of using the anion represented by the general formula (IV) as the anionic moiety of the color material of the present invention, the color of the color material can be adjusted to a desired color, depending on the combination with the cationic moiety.

The aromatic group at each of $Ar^2$ and $Ar^3$ is not particularly limited. The aromatic group may be an aromatic hydrocarbon group having a carbon ring or a heterocyclic ring. Examples of the aromatic hydrocarbon group include: a benzene ring; condensed polycyclic aromatic hydrocarbon groups such as a naphthalene ring, a tetralin ring, an indene ring, a fluorene ring, an anthracene ring and a phenanthrene ring; and chain polycyclic hydrocarbon groups such as biphenyl, terphenyl, diphenylmethane, triphenylmethane and stilbene. The chain polycyclic hydrocarbon group may have a hetero atom such as O and S in the chain skeleton, such as diphenyl ether, etc. On the other hand, examples of the heterocyclic ring include: five-membered heterocyclic rings such as furan, thiophene, pyrrol, oxazole, thiazole, imidazole and pyrazole; six-membered heterocyclic rings such as pyran, pyrone, pyridine, pyrone, pyridazine, pyrimidine and pyrazine; and condensed polycyclic heterocyclic rings such as benzofuran, thionaphthene, indole, carbazole, coumalin, benzo-pyrone, quinoline, isoquinoline, acridine, phthalazine, quinazoline and quinoxaline. These aromatic groups may have a substituent.

As the substituent of the aromatic group, an alkyl group having 1 to 5 carbon atoms and a halogen atom can be exemplified.

Each of $Ar^2$ and $Ar^3$ is preferably an aromatic group having 6 to 20 carbon atoms, more preferably an aromatic group having a condensed polycyclic carbon ring having 10 to 14 carbon atoms. Particularly, from the point of view that the structure is simple and the raw materials are low-cost, still more preferred are a phenylene group and a naphthalene group.

In the general formula (III), "Q" is a direct bond or a divalent linking group. Examples of the divalent linking group include an alkylene group having 1 to 10 carbon atoms, an arylene group, a —CONH— group, a —COO— group, an ether group having 1 to 10 carbon atoms (—R'—OR"—: each of R' and R" is independently an alkylene group), and a combination thereof. Of them, "Q" is preferably a direct bond or a —COO— group.

In the general formula (III), is not particularly limited as long as it is an integer of 1 or more. From the viewpoint of availability of raw materials, "f" is preferably 1.

In the general formula (III), "g" is an integer of 2 or more. Particularly, from the viewpoint of heat resistance, "g" is preferably 50 or more, more preferably 80 or more. On the other hand, from the viewpoint of solubility, "g" is preferably 3,000 or less, more preferably 2,000 or less. The weight average molecular weight of the general formula (III) is preferably from 10,000 to 100,000. Herein, the weight average molecular weight means a standard polystyrene-equivalent weight average molecular weight measured by GPC (gel permeation chromatography).

In the general formula (III), the constitutional units may be all the same, or two or more kinds of units may be contained. In the general formula (III), the sum of "f"s equals to "c" in the general formula (I).

On the other hand, in the case that $B^{c-}$ is an inorganic anion, the structure and composition of the inorganic anion is not particularly limited as long as it is an inorganic oxo acid or a dehydration condensation thereof. Examples of the inorganic anion include: divalent or higher anions of an oxo acid such as a phosphate ion, a sulfate ion, a chromate ion, a tungstate ion ($WO_4^{2-}$) and a molybdate ion ($MoO_4^{2-}$); a polyacid ion obtained by a condensation of oxo acids; and mixtures thereof.

The polyacid ion may be an isopolyacid ion $(M_mO_n)^{c-}$ or a heteropolyacid ion $(X_iM_mO_n)^{c-}$. In the above ionic formula, represents a poly atom, "X" represents a hetero atom, "m" represents a composition ratio of the poly atom, and "n" represents a composition ratio of the oxygen atom. Examples of the poly atom "M" include Mo, W, V, Ti and Nb. Examples of the hetero atom "X" include Si, P, As, S, Fe and Co.

Particularly, from the viewpoint of heat resistance, preferred is an anion of an inorganic acid containing molybdenum (Mo) and/or tungsten (W).

Examples of the anion of the inorganic acid containing molybdenum and/or tungsten include: isopolyacids such as a tungstate ion $[W_{10}O_{32}]^{4-}$ and a molybdate ion $[Mo_6O_{19}]^{2-}$; and heteropolyacids such as a phosphotungstate ion $[PW_{12}O_{40}]^{3-}$, a tungstosilicate ion $[SiW_{12}O_{40}]^{4-}$, a phosphomolybdate ion $[PW_{12-x}Mo_xO_{40}]^{3-}$, a $H_3[PW_{2-x}Mo_xO_7]^{4-}$. Of the above, from the viewpoint of heat resistance and availability of raw materials, the anion of the inorganic acid containing molybdenum and/or tungsten is preferably a heteropolyacid, more preferably a heteropolyacid containing P (phosphorus).

In the general formula (I), "a" refers to the of cationic color-forming moieties constituting a cation. In the general formula (I), "a" is an integer of 2 or more. In the color material of the present invention, the cation is divalent or higher, and the anion is also divalent or higher; therefore, the molecular association described above is formed, resulting in an increase in heat resistance. On the other hand, the upper limit of "a" is not particularly limited. From the viewpoint of ease of production, "a" is preferably 4 or less, more preferably 3 or less.

In the general formula (I), "b" refers to the number of molecules of cation in the molecular association, and "d" refers to the number of molecules of anion in the molecular association. In the general formula (I), each of "b" and "d" is an integer of 1 or more. In the crystal or aggregate of the color material of the present invention, each of "b" and "d" is not limited to 1 and can be any natural number of 2 or more, such as 2, 3, 4 or so on. From the viewpoint of heat resistance, it is preferable that at least a part of the color material of the present invention forms a molecular association in which b≥2. In addition, from the viewpoint of heat resistance, it is preferable that at least a part of the color material of the present invention forms a molecular association in which d≥2.

When "b" is 2 or more, the cations in the molecular association may be of a single kind or a combination of two or more kinds. When "d" is 2 or more, the anions in the molecular association may be a single kind or a combination of two or more kinds, and a combination of an organic anion and an inorganic anion may also be used.

The color material of the present invention may be dissolved in a solvent and used. Examples of the solvent which dissolves the color material of the present invention include N-methylpyrrolidone (NMP), γ-butyrolactone, dimethyl sulfoxide (DMSO) and N,N-dimethylformamide (DMF).

On the other hand, the color material of the present invention can be used by dispersing the color material in a solvent having a solubility of the color material of 0.1 (mg/10 g solvent) or less at 23° C., that is, a solvent which is substantially insoluble or hardly soluble. In this case, the color material is dispersed in the solvent, with keeping its aggregation state. Hence, the heat resistance of the color material with keeping its molecular association state in the solvent is higher compared to the case of dissolving the color material in the solvent. Of the solvents described above, preferred is a solvent having a solubility of the color material of 0.01 (mg/10 g solvent) or less at 23° C., more preferred is a solvent in which the color material is substantially insoluble.

In the case where the color material used in the present invention is a normal salt, problems such as non-smooth dispersion or liquid dispersion gelation during storage, which are shown in the case of using an acid salt, may be not caused, resulting in high dispersion properties and high dispersion stability.

In the present invention, the solvent having a solubility of the color material represented by the general formula (I) of 0.1 (mg/10 g solvent) or less at 23° C., can be simply determined by the following evaluation method.

First, 10 g of a solvent to be evaluated and then 0.1 g of the color material are put in a 20 mL sample tube. The tube is covered with a lid, shaken well for 20 seconds, and then left in a water bath at 23° C. for 10 minutes. Then, 5 g of the supernatant is filtered to remove insoluble substances. The thus-obtained filtrate is diluted by 1,000 times. Then, the diluted solution is measured for absorption spectrum, using a 1 cm cell in an ultraviolet and visible spectrophotometer (product name: UV-2500PC; manufactured by: Shimadzu Corporation) to calculate the absorbance at the maximum absorption wavelength. At this time, if the absorbance at the maximum absorption wavelength is less than 2, it can be evaluated that the solvent is a solvent having a solubility of the color material represented by the general formula (I) of 0.1 (mg/10 g solvent) or less at 23° C. (that is, a hardly-soluble solvent).

Also, in the above evaluation method, the absorption spectrum is measured in the same manner as described above, without diluting the obtained filtrate, to calculate the absorbance at the maximum absorption wavelength. At this time, if the absorbance at the maximum absorption wavelength is less than 2, it can be evaluated that the solvent is a solvent which does not substantially dissolve the color material represented by the general formula (I).

The solvent having a solubility of the color material of 0.1 (mg/10 g solvent) or less at 23° C. is not particularly limited as long as it is a solvent which does not substantially dissolve the color material. The examples include ester solvents such as ethyl acetate, butyl acetate, methyl methoxypropionate, ethyl ethoxypropionate, ethyl lactate, methoxyethyl acetate, propylene glycol monomethyl ether acetate, 3-methoxy-3-methyl-1-butyl acetate, 3-methoxybutyl acetate, methoxybutyl acetate, ethoxyethyl acetate and ethyl cellosolve acetate.

<Method for Producing Color Material Represented by General Formula (I)>

The method for producing the color material represented by the general formula (I) is not particularly limited. For example, it can be obtained by producing a cationic moiety by the following method, and then introducing a counter anion.

As one method, the method for producing the color material represented by the following general formula (I) of the present invention comprises the step of: performing a condensation reaction between a compound represented by the following general formula (A) and a compound represented by the following general formula (B):

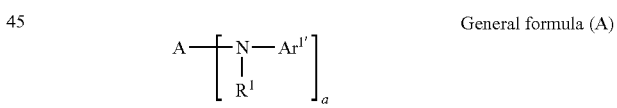

General formula (A)

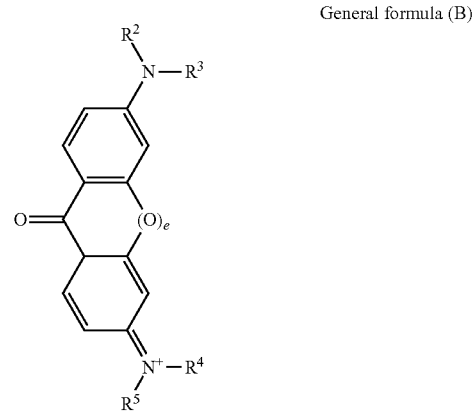

General formula (B)

-continued

General formula (I)

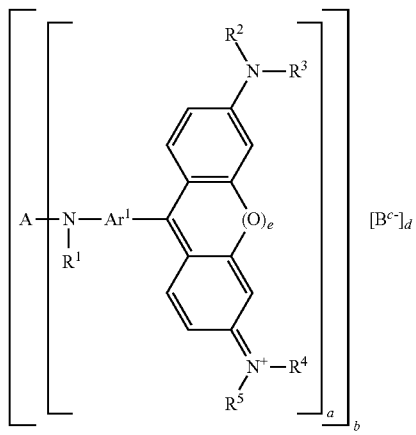

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N may be contained in a carbon chain of the organic group; $B^{c-}$ is a "c"-valent anion; each of $R^1$ to $R^5$ is independently a hydrogen atom, an alkyl group which may have a substituent, or an aryl group which may have a substituent; $R^2$ and $R^3$ may be bound to form a ring structure, and/or $R^4$ and $R^5$ may be bound to form a ring structure; $Ar^1$ is a divalent aromatic group which may have a substituent; $Ar^{1'}$ is a monovalent aromatic group in which a hydrogen atom is bound to $Ar^1$; $R^1$s may be the same or different; $R^2$s may be the same or different; $R^3$s may be the same or different; $R^4$s may be the same or different; $R^5$s may be the same or different; and $Ar^1$s may be the same or different; and wherein each of "a" and "c" is an integer of 2 or more; each of "b" and "d" is an integer of 1 or more; "e" is 0 or 1 and there is no bond when "e" is 0; and "e"s may be the same or different.

In the method for producing the color material of the present invention, by dehydration condensation performed between $Ar^{1'}$ in the general formula (A) and a carbonyl group in the general formula (B), a triarylmethane skeleton or a xanthene skeleton substituted with an aromatic group is formed and at the same time, a linking group A is introduced. According to said production method, the color materials having a different degree of polymerization are not produced. Also, unreacted substances have largely different skeletons, so that the separation is easy. Therefore, the color material of the present invention can be obtained in high purity and high yield.

(Compound Represented by General Formula (A))

First, the compound represented by the following general formula (A), which is a precursor compound of the cationic moiety, is synthesized. As the compound represented by the general formula (A), any of commercial products may be used:

General formula (A)

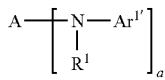

wherein "A", $R^1$ and "a" are the same as those in the general formula (I); and $Ar^{1'}$ is a structure in which a hydrogen is bound to $Ar^1$ of the general formula (I).

The method for synthesizing the compound represented by the general formula (A) is not particularly limited. For example, the compound can be obtained by reacting in a solvent a halogenated aromatic compound having a desired substituent $Ar^{1'}$ introduced therein, with an "a"-valent amine compound having a desired substituent A introduced therein, in the presence of a base and a catalyst such as palladium acetate.

The amount of the halogenated aromatic compound used in the above reaction varies, depending on a desired valence (a). For example, if "a" is desired to be 2, the amount of the halogenated aromatic compound is preferably 1.5 to 10 molar equivalent, more preferably 1.5 to 3.0 molar equivalent, still more preferably 1.8 to 2.2 molar equivalent, with respect to the amine compound, from the viewpoint of inhibiting generation of by-products and improving the reaction yield.

In the above reaction, the reaction temperature is not particularly limited and is generally around 100 to 150° C. It is preferably 130 to 145° C. from the viewpoint of inhibiting side reactions. Also in the above reaction, the reaction pressure is not particularly limited. It is preferably from an ordinary pressure to 0.1 MPa, more preferably an ordinary pressure. In the above reaction, the reaction time varies depending on the synthesis amount and the reaction temperature. It is generally set in the range from 6 to 72 hours, preferably from 6 to 48 hours.

The base used in the reaction is not particularly limited. The examples include sodium hydroxide, potassium hydrate, potassium carbonate, metal alkoxides and metal amides. Particularly, it is preferable to use a strong base with low nucleophilicity, from the viewpoint of inhibiting side reactions and improving the yield of the base generator. The examples include potassium t-butoxide, sodium t-butoxide, lithium t-butoxide, lithium diisopropylamide, potassium hexamethyldisilazide and lithium tetramethylpiperidide. Of them, potassium t-butoxide is more preferable for use.

The amount of the base added is not particularly limited. With respect to the amine compound, it is generally 2.0 to 4.0 molar equivalent. From the viewpoint of improving the reaction yield, it is preferably 2.5 to 3.5 molar equivalent.

(Synthesis of Cationic Moiety)

The cationic moiety of the color material represented by the general formula (I) is synthesized by performing a condensation reaction between the compound represented by the general formula (A) and the compound represented by the following general formula (B). For example, the cationic moiety can be obtained in the form of a chloride by reacting the compound represented by the general formula (A) and the compound represented by the following general formula (B) in a solvent, using a chlorinating agent such as phosphorous oxychloride. As the compound represented by the following general formula (B), any of commercial products can be used:

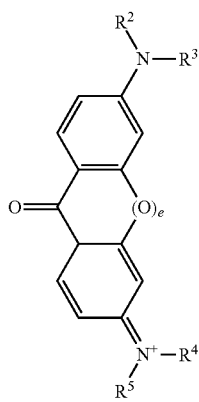

General formula (B)

wherein $R^2$ to $R^5$ and "e" are the same as those in the general formula (I).

The amount of the compound represented by the general formula (B) used in the above reaction varies depending on a desired valence (a). For example, if "a" is desired to be 2, the amount of the compound represented by the general formula (B) is preferably 1.5 to 4.0 molar equivalent, more preferably 1.5 to 3.0 molar equivalent, still more preferably 1.8 to 2.2 molar equivalent, with respect to the compound represented by the general formula (A), from the viewpoint of inhibiting generation of by-products and improving the reaction yield.

The reaction temperature in the above reaction is not particularly limited, and is generally around 110 to 150° C. It is preferably 110 to 120° C., from the viewpoint of inhibiting side reactions. The reaction pressure in the above reaction is not particularly limited. It is preferably from an ordinary pressure to 0.1 MPa, more preferably an ordinary pressure. The reaction time in the above reaction varies depending on the amount of synthesis and the reaction temperature. It is generally set in the range from 1 to 10 hours, preferably 1 to 5 hours.

The amount of the phosphorous oxychloride added is not particularly limited. With respect to the compound represented by the general formula (A), it is generally 1.5 to 3.0 molar equivalent. From the viewpoint of improving the reaction yield, it is preferably from 1.8 to 3.0 molar equivalent.

The color material represented by the general formula (I) can be obtained by mixing the chloride of the cationic moiety obtained by the above reaction and a desired anionic moiety in a solvent.

EXAMPLES

Hereinafter, the present invention will be explained in detail, with reference to examples. The scope of the present invention is not restricted by these examples, however.

Synthesis Example

Synthesis of Intermediate 1

First, 18.7 g (73.4 mmol) of 1-iodonaphthalene, 9.88 g (102.8 mmol) of sodium tert-butoxide (both manufactured by: Wako Pure Chemical Industries, Ltd.), 5.0 g (36.7 mmol) of p-xylenediamine (manufactured by: Tokyo Chemical Industry Co., Ltd.), 0.27 g (0.57 mmol) of 2-dicyclohexylphosphino-2',4',6'-triisopropylbiphenyl (manufactured by: Aldrich) and 0.054 g (0.28 mmol) of palladium acetate (manufactured by: Wako Pure Chemical Industries, Ltd.) were dispersed in 36 mL of xylene and reacted at 130 to 135° C. for 24 hours. After the reaction, the resultant was cooled to room temperature. Crystals thus precipitated were filtered and then washed with methanol. Next, the crystals were washed with water and dried to obtain 9.79 g (yield 69%) of intermediate 1 represented by the following chemical formula (1).

From the following analysis result, the obtained compound was confirmed to be a desired compound.

MS (ESI) (m/z): 389(+)

Values of elemental analysis: CHN actual measurement values (86.72%, 6.54%, 6.97%); theoretical values (86.56%, 6.23%, 7.21%)

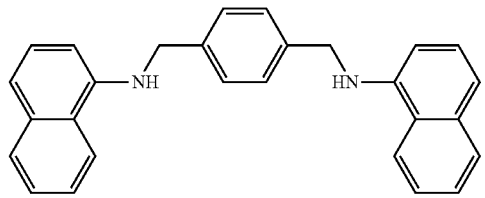

Chemical formula (1)

Synthesis Example

Synthesis of Intermediate 2

First, 10.0 g (25.7 mmol) of intermediate 1, 100 mL of toluene, 7.89 g (51.5 mmol) of phosphorous oxychloride (manufactured by: Wako Pure Chemical Industries, Ltd.) were mixed and agitated. Next, 16.2 g (49.9 mmol) of 4,4'-bis(diethylamino)benzophenone (manufactured by: Tokyo Chemical Industry Co., Ltd.) was added in the mixture, and the mixture was refluxed for 5 hours and cooled. After the reaction, the toluene was decanted. Then, 100 mL of water was added thereto, and the mixture was filtered to obtain a cake (a resinous precipitate). The thus-obtained cake was dispersed in dilute hydrochloric acid. The dispersion was filtered, and a residue thus obtained was washed with water and then dried to obtain 18.4 g (yield 66%) of intermediate 2 represented by the following chemical formula (2).

From the following analysis result, the obtained compound was confirmed to be a desired compound.

MS (ESI) (m/z): 501(+), divalent

Values of elemental analysis: CHN actual measurement values (78.02%, 7.13%, 7.11%); theoretical values (78.26%, 7.32%, 7.82%)

Chemical Formula (2)

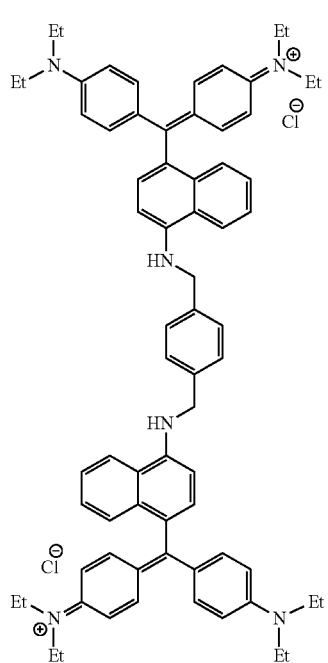

Example 1

Synthesis of Color Material A

First, 1.03 g (3.10 mmol) of disodium 2,6-naphthalenedisulfonate (manufactured by: Tokyo Chemical Industry Co., Ltd.), 30 mL of methanol and 20 mL of water were mixed and agitated at 50 to 55° C. Next, 3.33 g (3.10 mmol) of intermediate 2 was added to the mixture, and the mixture was stirred at 50 to 55° C. for hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 3.37 g (yield 84%) of color material A represented by the following chemical formula (3).

From the following analysis result, the obtained compound was confirmed to be a desired compound.

(ESI) (m/z): 502(+), divalent, 143(−), divalent

Values of elemental analysis: CHN actual measurement values (74.68%, 6.63%, 6.21%); theoretical values (74.50%, 6.56%, 6.52%)

Chemical Formula (3)

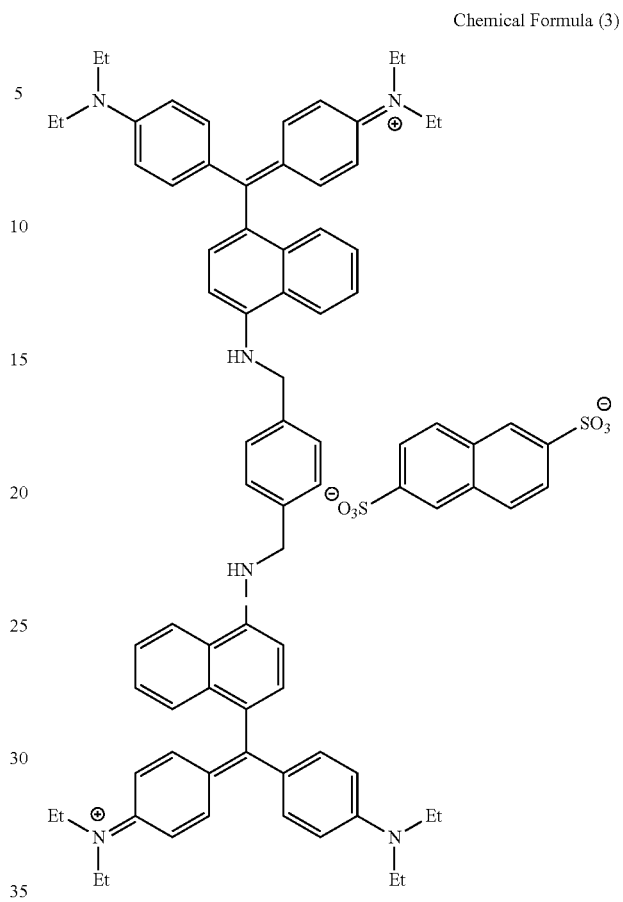

Example 2

Synthesis of Color Material B

First, 0.92 g (2.12 mmol) of trisodium 1,3,6-Naphthalenetrisulfonate (manufactured by: Tokyo Chemical Industry Co., Ltd.), 40 mL of methanol and 20 mL of water were mixed and agitated at 50 to 55° C. Next, 3.44 g (3.20 mmol) of intermediate 2 was added thereto, and the mixture was agitated at 50 to 55° C. for hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 3.12 g (yield 78%) of color material B represented by the following chemical formula (4).

From the following analysis result, the obtained compound was confirmed to be a desired compound.

MS (ESI) (m/z): 502(+), divalent, 121(−), trivalent

Values of elemental analysis: CHN actual measurement values (73.97%, 6.62%, 6.91%); theoretical values (73.84%, 6.57%, 6.74%)

Chemical Formula (4)

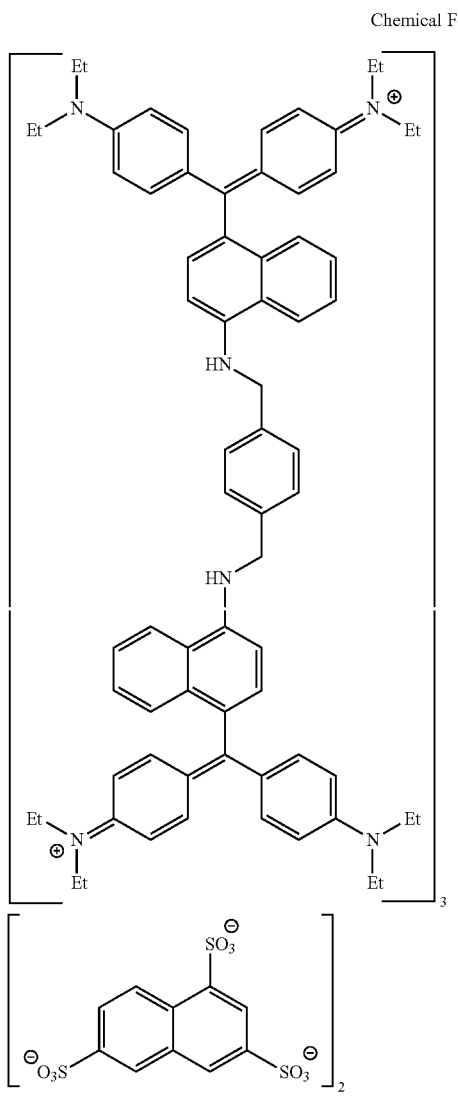

Chemical Formula (5)

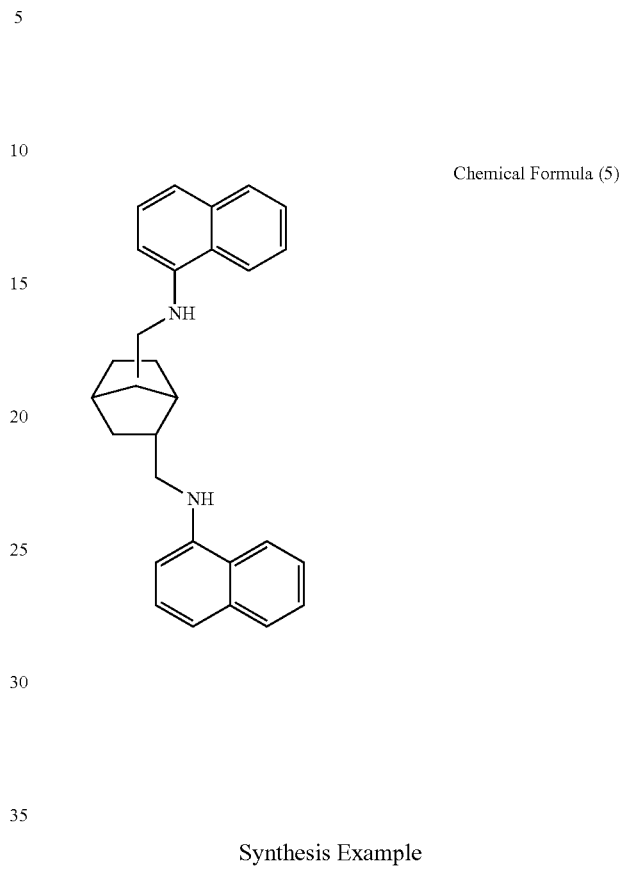

Synthesis Example

Synthesis of Intermediate 3

First, 15.2 g (60 mmol) of 1-iodonaphthalene (manufactured by: Wako Pure Chemical Industries, Ltd.), 4.63 g (30 mmol) of norbornane diamine (NBDA) (CAS No. 56602-77-8) (manufactured by: Mitsui Chemicals, Inc.), 8.07 g (84 mmol) of sodium-tert-butoxide, 0.09 g (0.2 mmol) of 2-dicyclohexylphosphino-2',6'-dimethoxybiphenyl (manufactured by: Aldrich) and 0.021 g (0.1 mmol) of palladium acetate (manufactured by: Wako Pure Chemical Industries, Ltd.) were dispersed in mL of xylene and reacted at 130 to 135° C. for 48 hours. After the reaction, the resultant was cooled to room temperature, and water was added thereto. An organic phase was extracted from the resultant, and dried with magnesium sulfate and then concentrated, thereby obtaining 8.5 g (yield 70%) of intermediate 3 represented by the following chemical formula (5).

From the following analysis result, the obtained compound was confirmed to be a desired compound.

MS (ESI) (m/z): 407(M+H)

Values of elemental analysis: CHN actual measurement values (85.47%, 8.02%, 6.72%); theoretical values (85.26%, 8.11%, 6.63%)

Synthesis Example

Synthesis of Intermediate 4

First, 8.46 g (20.8 mmol) of intermediate 3, 13.5 g (41.6 mmol) of 4,4'-bis(dimethylamino)benzophenone (manufactured by: Tokyo Chemical Industry Co., Ltd.) and 60 mL of toluene were mixed and agitated at 45 to 50° C. Next, 6.38 g (51.5 mmol) of phosphorous oxychloride (manufactured by: Wako Pure Chemical Industries, Ltd.) was added dropwise to the mixture, and the mixture was refluxed for 2 hours and then cooled. After the reaction, the toluene was decanted. A resinous precipitate thus obtained was dissolved by adding 40 mL of chloroform, 40 mL of water and concentrated hydrochloric acid to separate a chloroform phase. The chloroform phase was washed with water, dried with magnesium sulfate and then concentrated. To the thus-obtained concentrated product, 65 mL of ethyl acetate was added and refluxed. After cooling, the thus-produced precipitate was filtered off to obtain 15.9 g (yield 70%) of intermediate 4 represented by the following chemical formula (6).

From the following analysis result, the obtained compound was confirmed to be a desired compound.

MS (ESI) (m/z): 511(+), divalent

Values of elemental analysis: CHN actual measurement values (78.13%, 7.48%, 7.78%); theoretical values (78.06%, 7.75%, 7.69%)

Chemical Formula (6)

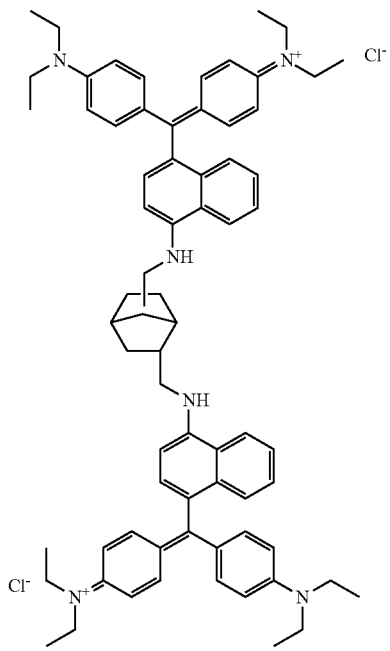

Example 3

Synthesis of Color Material C

First, 1.27 g (2.93 mmol) of trisodium 1,3,6-naphthalenetrisulfonate (manufactured by: Tokyo Chemical Industry Co., Ltd.), 40 mL of methanol and 48 mL of water were mixed and agitated at 50 to 55° C. Next, 3.44 g (3.20 mmol) of intermediate 4 was added thereto, and the mixture was agitated at 50 to 55° C. for hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 4.9 g (yield 89%) of color material B represented by the following chemical formula (7).

From the following analysis result, the obtained compound was confirmed to be a desired compound.

MS (ESI) (m/z): 511(+), divalent, 121(−), trivalent

Values of elemental analysis: CHN actual measurement values (74.01%, 6.99%, 6.47%); theoretical values (73.74%, 6.96%, 6.54%)

Chemical formula (7)

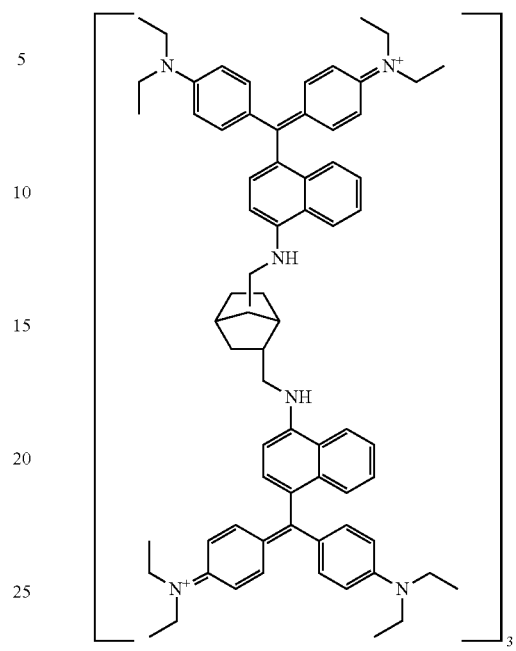

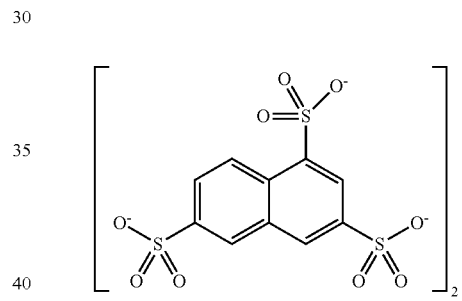

Example 4

Synthesis of Color Material D

First, 1.48 g (1.9 mmol) of Direct Blue 86 (manufactured by: Tokyo Chemical Industry Co., Ltd.), mL of methanol and 20 mL of water were mixed and agitated at 50 to 55° C. Next, 2.00 g (1.83 mmol) of intermediate 4 was added thereto, and the mixture was agitated at 50 to 55° C. for 1 hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 1.60 g (yield 50%) of color material D represented by the following chemical formula (8).

From the following analysis result, the obtained compound was confirmed to be a desired compound.

MS (ESI) (m/z): 510(+), divalent, 369(−), divalent

Values of elemental analysis: CHN actual measurement values (70.41%, 5.80%, 10.94%); theoretical values (70.30%, 5.84%, 11.14%)

Chemical Formula (8)

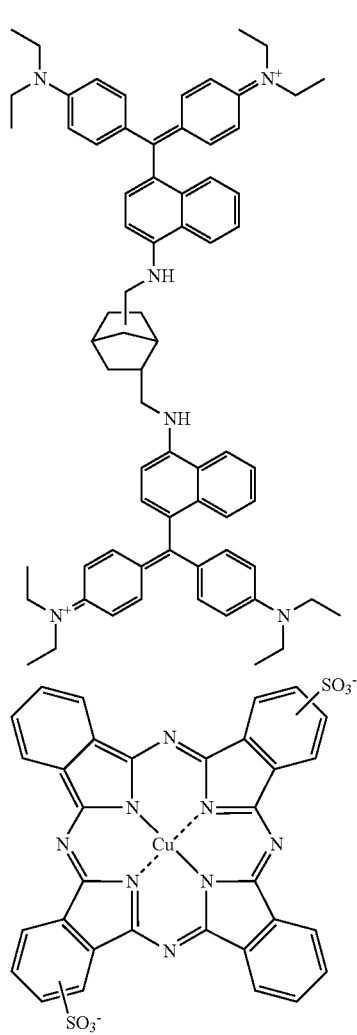

Chemical formula (9)

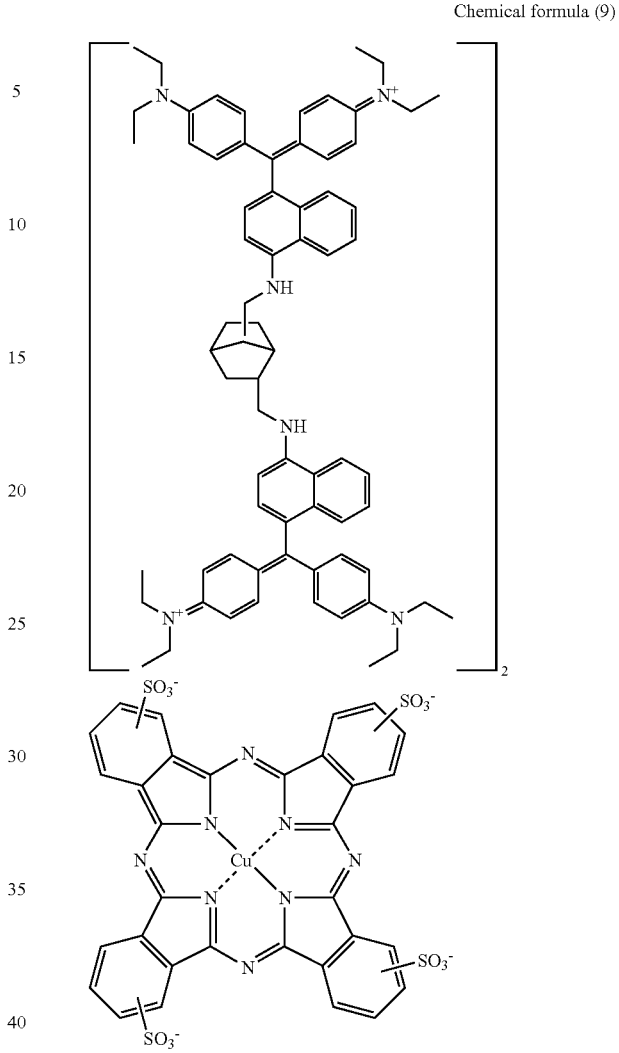

Example 5

Synthesis of Color Material E

First, 2.0 g (1.00 mmol) of copper(II) phthalocyanine tetrasulfonic acid tetrasodium salt (manufactured by: Aldrich), 100 mL of methanol and 40 mL of water were mixed and agitated at 50 to 55° C. Next, 2.0 g (1.83 mmol) of intermediate 4 was added thereto, and the mixture was agitated at 50 to 55° C. for hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 2.4 g (yield 89%) of color material E represented by the following chemical formula (9).

From the following analysis result, the obtained compound was confirmed to be a desired compound.

MS (ESI) (m/z): 510(+), divalent, 224(−), tetravalent

Values of elemental analysis: CHN actual measurement values (64.32%, 5.41%, 10.11%); theoretical values (64.44%, 5.36%, 10.21%)

Example 6

Synthesis of Color Material F

First, 2.76 g of poly(sodium 4-styrenesulfonate) (weight average molecular weight (Mw) up to 70,000, 30 wt % aqueous solution) (manufactured by: Aldrich), 100 mL of methanol and 50 mL of water were mixed and agitated at 50 to 55° C. Next, 2.0 g (1.83 mmol) of intermediate 4 was added thereto, and the mixture was agitated at 50 to 55° C. for 1 hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 2.1 g (yield 82%) of color material F represented by the following chemical formula (10).

From the following analysis result, the obtained compound was confirmed to be a desired compound.

MS (ESI) (m/z): 510(+), divalent

Values of elemental analysis: CHN actual measurement values (75.87%, 7.17%, 6.25%); theoretical values (75.18%, 7.25%, 6.05%)

Chemical Formula (10)

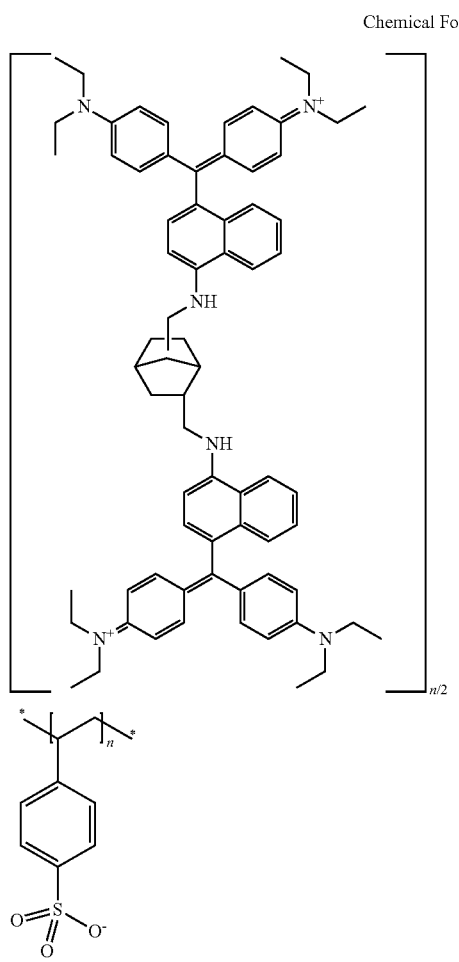

Example 7

Synthesis of Color Material G

First, 0.92 g (2.12 mmol) of trisodium 1,3,6-naphthalenetrisulfonate (manufactured by: Tokyo Chemical Industry Co., Ltd.), 0.48 g of poly(sodium 4-Styrenesulfonate) (weight average molecular weight (Mw) up to 70,000, 30 wt % aqueous solution), 40 mL of methanol and 20 mL of water were mixed and agitated at 50 to 55° C. Next, 3.44 g (3.20 mmol) of intermediate 4 was added thereto, and the mixture was agitated at 50 to 55° C. for 1 hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 2.43 g (yield 59%) of color material G represented by the following chemical formula (11).

From the following analysis result, the obtained compound was confirmed to be a desired compound.

MS (ESI) (m/z): 510(+), divalent, 121(−), trivalent

Values of elemental analysis: CHN actual measurement values (74.22%, 7.34%, 6.21%); theoretical values (74.04%, 7.15%, 6.48%)

Chemical Formula (11)

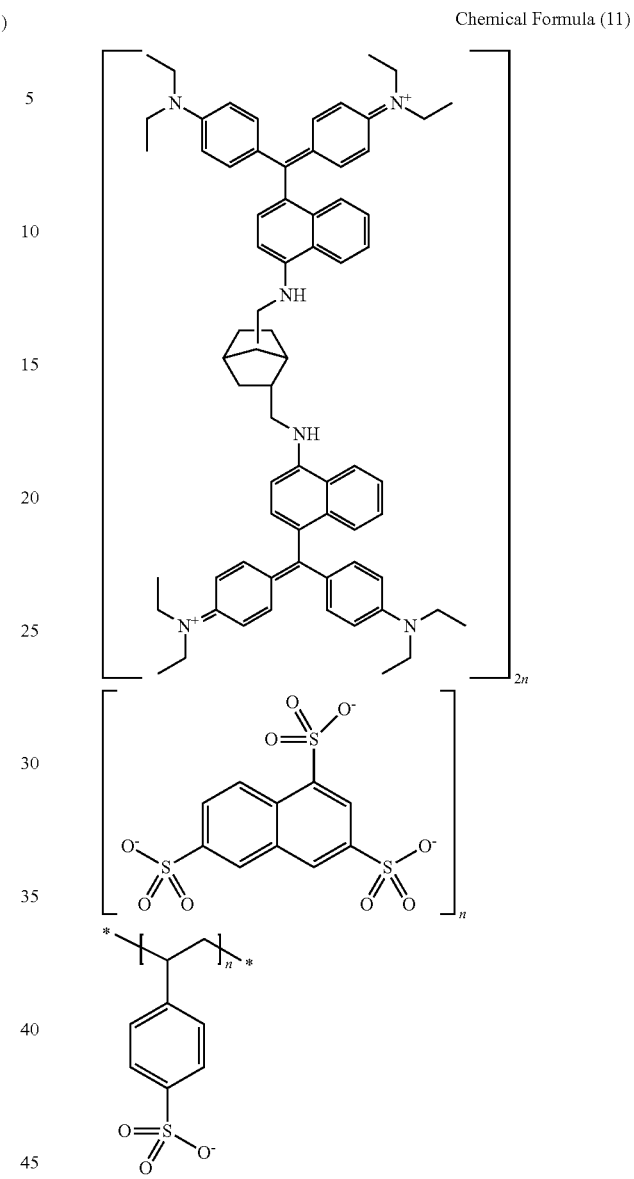

Example 8

Synthesis of color Material H

First, 4.65 g (2.01 mmol) of 12-molybdo phosphoric acid n-hydrate (manufactured by: KANTO CHEMICAL CO., INC.), 40 mL of methanol and 20 mL of water were mixed and agitated at 50 to 55° C. Next, 3.0 g (2.75 mmol) of intermediate 4 was added thereto, and the mixture was agitated at 50 to 55° C. for 1 hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 5.6 g (yield 91%) of color material H represented by the following chemical formula (12).

From the following analysis result, the obtained compound was confirmed to be a desired compound.

MS (ESI) (m/z): 510(+), divalent, 607(−), trivalent

Values of elemental analysis: CHN actual measurement values (52.34%, 5.44%, 5.23%); theoretical values (52.13%, 5.61%, 5.14%)

Chemical Formula (12)

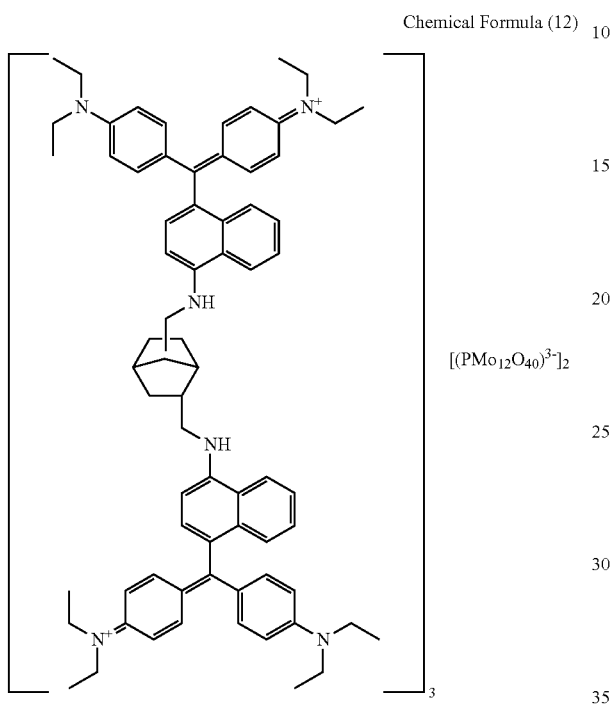

[(PMo$_{12}$O$_{40}$)$^{3-}$]$_2$

Example 9

Synthesis of Color Material I

First, 6.16 g (18.67 mmol) of sodium tungstate dihydrate (manufactured by: Aldrich), 1.13 g (4.67 mmol) of sodium molybdate dihydrate (manufactured by: Aldrich), 0.35 g (1.945 mmol) of sodium phosphate dibasic dehydrate, and 60 mL of water were mixed and acidified with hydrochloric acid. Next, a small amount of zinc powder was added thereto and agitated at 90 to 95° C. To this mixture, a methanol solution (40 mL) of 4.25 g (3.89 mmol) intermediate 4 was added and agitated at 50 to 55° C. for 1 hour. Then, 100 mL of water was added thereto, and the mixture was filtered to obtain a precipitate. The precipitate was washed with water. The thus-obtained cake was dried to obtain 7.1 g (yield 94%) of color material I represented by the following chemical formula (13).

From the following analysis result, the obtained compound was confirmed to be a desired compound.

MS (ESI) (m/z): 510(+), divalent

Values of elemental analysis: CHN actual measurement values (41.55%, 5.34%, 4.32%); theoretical values (41.66%, 5.17%, 4.11%)

Chemical Formula (13)

$$\left( H_3 \left( P \left( \begin{array}{l} W_2O_7;\ 80\% \\ Mo_2O_7;\ 20\% \end{array} \right)_6 \right) \right)^{4-}$$

Comparative Example 1

Synthesis of Color Material J

First, 1.15 g (5.94 mmol) of Sodium p-toluenesulfonate (manufactured by: Tokyo Chemical Industry Co., Ltd.), 33 mL of methanol and 33 mL of water were mixed and agitated at 50 to 55° C. Next, 3.19 g (2.97 mmol) of intermediate 2 was added thereto, and the mixture was agitated at 50 to 55° C. for 1 hour. The solution was concentrated by means of an evaporator to evaporate the methanol, and 100 mL of water was added thereto. The mixture was filtered to obtain a precipitate, and the precipitate was washed with water. The thus-obtained cake was dried to obtain 3.33 g (yield 83%) of color material J represented by the following chemical formula (14).

From the following analysis result, the obtained compound was confirmed to be a desired compound.

MS (ESI) (m/z): 502(+), divalent, 171(−), monovalent

Values of elemental analysis: CHN actual measurement values (75.18%, 7.11%, 6.15%); theoretical values (74.97%, 6.89%, 6.24%)

Chemical Formula (14)

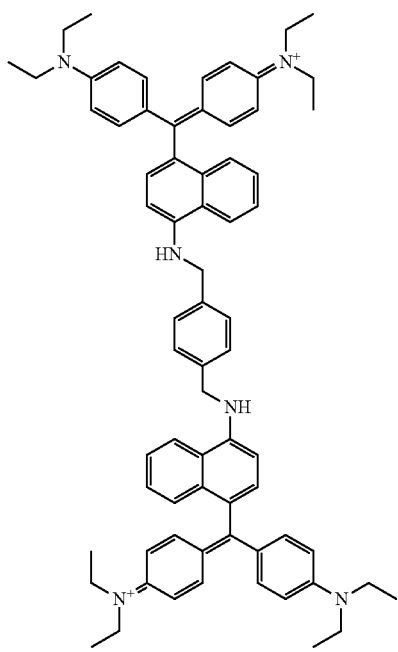

Comparative Example 2

Synthesis of Color Material K

First, 1.62 g (50.2 mmol) of disodium naphthalene 2,6-sulfonate (manufactured by: Tokyo Chemical Industry Co., Ltd.) was dissolved by heating at 50 to 55° C. in a mixture of 50 mL of methanol and 50 mL of water. Then, 5 g (97.3 mmol) of Basic Blue 7 (CI-42595) (manufactured by: Tokyo Chemical Industry Co., Ltd.) was added thereto, and the mixture was agitated at the same temperature for 1 hour. The solution was concentrated by means of an evaporator to evaporate the methanol, and 100 mL of water was added thereto. The mixture was filtered to obtain a precipitate, and the precipitate was washed with water. The thus-obtained cake was dried under pressure to obtain 5.2 g (yield 86%) of color material K represented by the following chemical formula (15).

From the following analysis result, the obtained compound was confirmed to be a desired compound.

MS (ESI) (m/z): 478(+), 143(2−), (divalent)

Values of elemental analysis: CHN actual measurement values (73.12%, 6.77%, 6.86%); theoretical values (73.40%, 6.97%, 6.76%)

Chemical Formula (15)

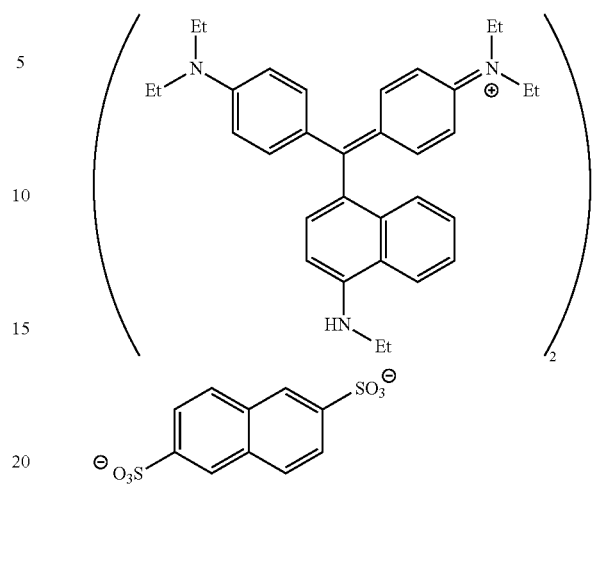

Comparative Example 3

Synthesis of Color Material L

First, 3.0 g (6.9 mmol) of trisodium naphthalene 1,3,6-sulfonate (manufactured by: Tokyo Chemical Industry Co., Ltd.) was dissolved by heating at 50 to 55° C. in a mixture of 100 mL of methanol and 100 mL of water. Next, 10.7 g (20.7 mmol) of Basic Blue 7 (CI-42595) (manufactured by: Tokyo Chemical Industry Co., Ltd.) was added thereto, and the mixture was agitated at the same temperature for 1 hour. The solution was concentrated by means of an evaporator to evaporate the methanol, and 30 mL of water was added thereto. The mixture was filtered to obtain a precipitate, and the precipitate was washed with water. The thus-obtained cake was dried under pressure to obtain 11.2 g (yield 90%) of color material L of Comparative example 3 represented by the following chemical formula (16).

From the following analysis result, the obtained compound was confirmed to be a desired compound.

MS (ESI) (m/z): 478(+), 122(3−), (trivalent)

Values of elemental analysis: CHN actual measurement values (72.88%, 6.78%, 6.85%); theoretical values (72.67%, 6.99%, 7.00%)

Chemical Formula (16)

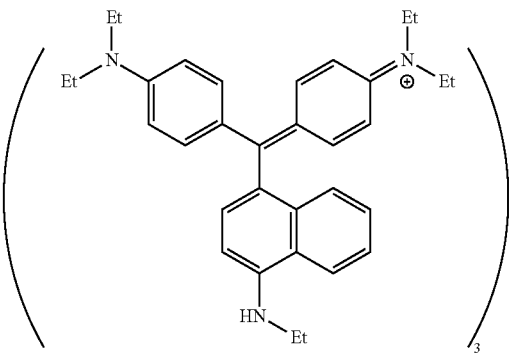

-continued

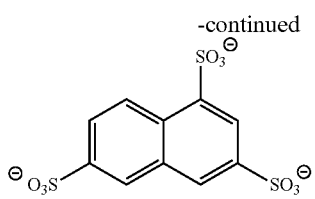

Comparative Example 4

Synthesis of Color Material M

First, 1.48 g (1.9 mmol) of Direct Blue 86 (manufactured by: Tokyo Chemical Industry Co., Ltd.) was dissolved by heating at 50 to 55° C. in a mixture of mL of methanol and 20 mL of water. Next, 1.95 g (3.8 mmol) of Basic Blue 7 (CI-42595) (manufactured by: Tokyo Chemical Industry Co., Ltd.) was added thereto, and the mixture was agitated at the same temperature for 1 hour. The solution was concentrated by means of an evaporator to evaporate the methanol, and 30 mL of water was added thereto. The mixture was filtered to obtain a precipitate, and the precipitate was washed with water. The thus-obtained cake was dried under pressure to obtain 2.9 g (yield 90%) of color material M represented by the following chemical formula (17).

From the following analysis result, the obtained compound was confirmed to be a desired compound.

MS (ESI) (m/z): 478(+), 369(−), (divalent)

Values of elemental analysis: CHN actual measurement values (64.02%, 4.73%, 12.89%); theoretical values (64.16%, 4.80%, 12.66%)

Chemical Formula (17)

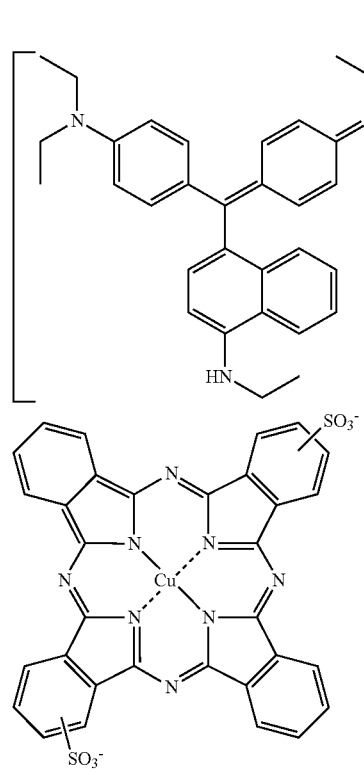

Comparative Example 5

Synthesis of Color Material N

First, 1.9 g (0.97 mmol) of copper(II) phthalocyanine tetrasulfonic acid tetrasodium salt (manufactured by: Aldrich) was dissolved by heating at 50 to 55° C. in a mixture of 40 mL of methanol and 20 mL of water. Next, 2.00 g (3.9 mmol) of Basic Blue 7 (CI-42595) (manufactured by: Tokyo Chemical Industry Co., Ltd.) was added thereto, and the mixture was agitated at the same temperature for 1 hour. The solution was concentrated by means of an evaporator to evaporate the methanol, and 30 mL of water was added thereto. The mixture was filtered to obtain a precipitate, and the precipitate was washed with water. The thus-obtained cake was dried under pressure to obtain 2.5 g (yield 92%) of color material N represented by the following chemical formula (18).

From the following analysis result, the obtained compound was confirmed to be a desired compound.

MS (ESI) (m/z): 478(+), 224(−), tetravalent

Values of elemental analysis: CHN actual measurement values (70.23%, 6.12%, 9.67%); theoretical values (70.02%, 6.38%, 9.96%)

Chemical Formula (18)

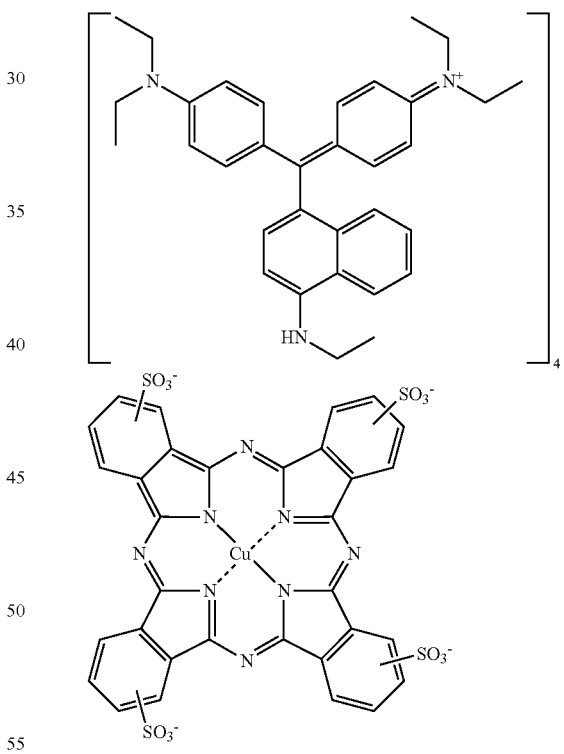

Comparative Example 6

Synthesis of Color Material O

First, 2.76 g of poly(sodium 4-Styrenesulfonate) (weight average molecular weight (Mw) up to 70,000, 30 wt % aqueous solution) (manufactured by: Aldrich) was dissolved by heating at 50 to 55° C. in a mixture of 40 mL of methanol and 20 mL of water. Next, 1.88 g (3.66 mmol) of Basic Blue 7 (CI-42595) (manufactured by: Tokyo Chemical Industry Co., Ltd.) was added thereto, and the mixture was agitated at the same temperature for 1 hour. The solution was concentrated by means of an evaporator to evaporate the methanol, and 30 mL of water was added thereto. The mixture was filtered to obtain a precipitate, and the precipitate was washed with water. The thus-obtained cake was dried under pressure to obtain 2.0 g (yield 82%) of color material O represented by the following chemical formula (19).

From the following analysis result, the obtained compound was confirmed to be a desired compound.

MS (ESI) (m/z): 478(+)

Values of elemental analysis: CHN actual measurement values (74.49%, 7.13%, 6.24%); theoretical values (74.29%, 7.30%, 6.34%)

Values of elemental analysis: CHN actual measurement values (73.24%, 7.25%, 6.77%); theoretical values (73.02%, 7.19%, 6.81%)

Chemical Formula (19)

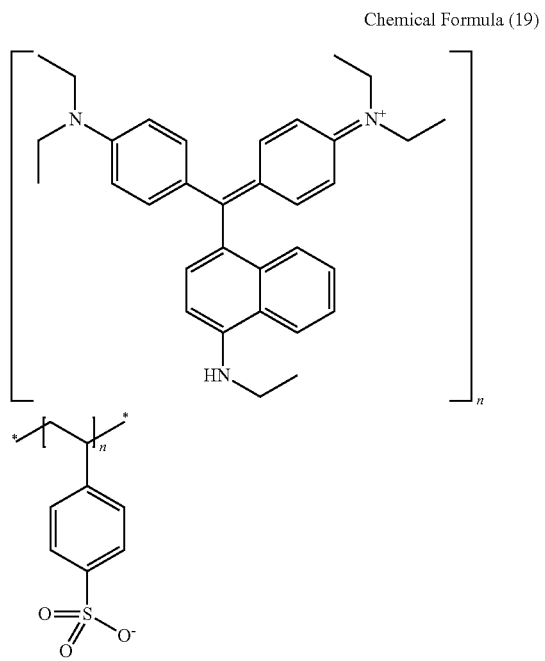

Chemical Formula (20)

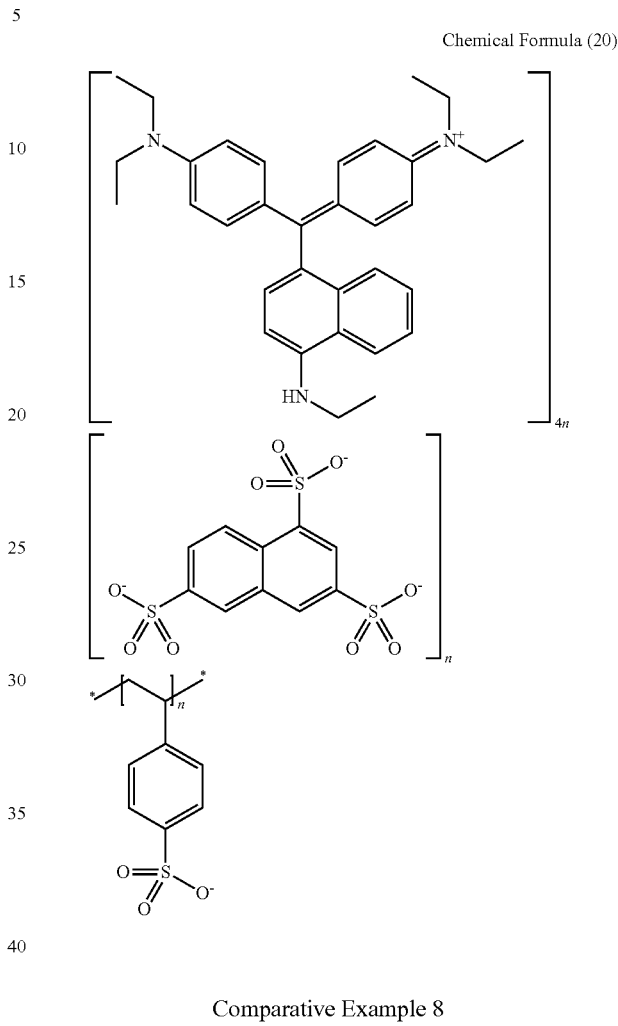

Comparative Example 7

Synthesis of Color Material P

First, 0.92 g (2.12 mmol) of Trisodium 1,3,6-naphthalenetrisulfonate and 0.48 g of poly(sodium 4-Styrenesulfonate) (weight average molecular weight (Mw) up to 70,000, 30 wt % aqueous solution) (both manufactured by: Tokyo Chemical Industry Co., Ltd.) were dissolved by heating at 50 to 55° C. in a mixture of mL of methanol and 20 mL of water. Next, 3.29 g (6.40 mmol) of Basic Blue 7 (CI-42595) (manufactured by: Tokyo Chemical Industry Co., Ltd.) was added thereto, and the mixture was agitated at the same temperature for 1 hour. The solution was concentrated by means of an evaporator to evaporate the methanol, and 30 mL of water was added thereto. The mixture was filtered to obtain a precipitate, and the precipitate was washed with water. The thus-obtained cake was dried under pressure to obtain 3.5 g (yield 84%) of color material P represented by the following chemical formula (20).

From the following analysis result, the obtained compound was confirmed to be a desired compound.

MS (ESI) (m/z): 478(+), 607(−), trivalent

Comparative Example 8

Synthesis of Color Material Q

First, 2.33 g (1.01 mmol) of 12-molybdo phosphoric acid n-hydrate (manufactured by: KANTO CHEMICAL CO., INC.) was dissolved by heating at 50 to 55° C. in a mixture of 40 mL of methanol and 20 mL of water. Next, 1.56 g (3.03 mmol) of Basic Blue 7 (CI-42595) (manufactured by: Tokyo Chemical Industry Co., Ltd.) was added thereto, and the mixture was agitate at the same temperature for 1 hour. The solution was concentrated by means of an evaporator to evaporate the methanol, and 30 mL of water was added thereto. The mixture was filtered to obtain a precipitate, and the precipitate was washed with water. The thus-obtained cake was dried under pressure to obtain 3.1 g (yield 93%) of color material Q represented by the following chemical formula (21).

From the following analysis result, the obtained compound was confirmed to be a desired compound.

MS (ESI) (m/z): 478(+), 607(−), trivalent

Values of elemental analysis: CHN actual measurement values (32.34%, 4.23%, 3.97%); theoretical values (32.26%, 4.33%, 3.84%)

Chemical Formula (21)

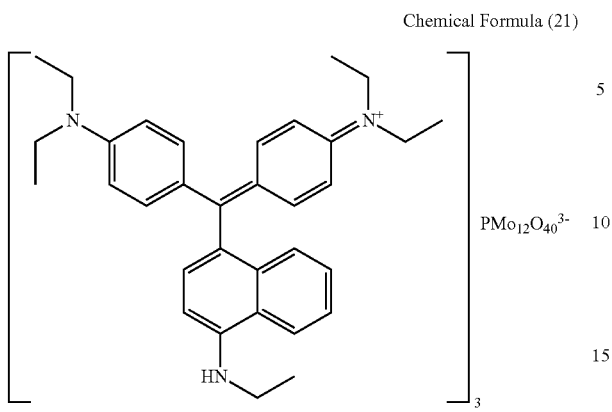

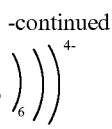

Comparative Example 9

Synthesis of Color Material R

First, 6.16 g (18.67 mmol) of sodium tungstate dihydrate (manufactured by: Aldrich), 1.13 g (4.67 mmol) of sodium molybdate dihydrate (manufactured by: Aldrich), 0.35 g (1.945 mmol) of sodium phosphate dibasic dehydrate, and 60 mL of water were mixed and acidified with hydrochloric acid. Next, a small amount of zinc powder was added thereto and agitated at 90 to 95° C. To this mixture, 4.0 g (7.78 mmol) of Basic Blue 7 (CI-42595) (manufactured by: Tokyo Chemical Industry Co., Ltd.) was added and agitated at the same temperature for 1 hour. The solution was concentrated by means of an evaporator to evaporate the methanol, and 30 mL of water was added thereto. The mixture was filtered to obtain a precipitate, and the precipitate was washed with water. The thus-obtained cake was dried under pressure to obtain 7.0 g (yield 96%) of color material R represented by the following chemical formula (22).

From the following analysis result, the obtained compound was confirmed to be a desired compound.

MS (ESI) (m/z): 478(+), 607(−), trivalent

Values of elemental analysis: CHN actual measurement values (33.97%, 5.13%, 4.24%); theoretical values (33.89%, 5.02%, 4.35%)

Chemical Formula (22)

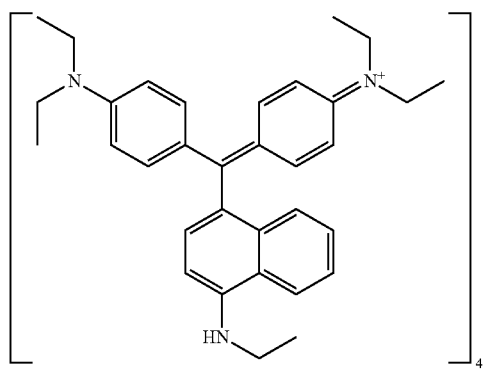

Comparative Example 10

Synthesis of Color Material S

In accordance with the method disclosed in Patent Literature 4, 12-molybdophosphate of a polysiloxane dye was synthesized to obtain color material S.

First, 51.52 g of Basic Blue 7 (BB7) (manufactured by: Tokyo Chemical Industry Co., Ltd.) was dissolved in 750 mL of ion-exchanged water. Then, an aqueous solution of 2N sodium hydroxide was added thereto, with agitation, until the depronated form of the dye was completely precipitated, no blue color remained in the solution and did not return for several hours. The thus-produced precipitate was filtered off, washed three times with ion-exchanged water, and then dried at 60° C. under reduced pressure (0.1 kPa). Therefore, 45.23 g (94.7%) of deprotonated BB7 was separated in the form of a nearly black powder.

Separately, 50 mL of 3-iodopropyl-trimethoxysilane (manufactured by: Sigma-Aldrich Japan K.K.) and 2.0 mL (2.95 g; 10.2 mmol) of anhydrous ethanol solution were mixed and then agitated at room temperature for 60 hours under an argon flow. Then, the solvent was distilled away under a reduced pressure to obtain 3-iodopropyl-triethoxysilane. The thus-obtained 3-iodopropyl-triethoxysilane was dissolved in 50 mL of anhydrous acetonitrile, and 2.389 g (5 mmol) of the above-mentioned deprotonated BB7 was added thereto. Then, under an argon flow, the thus-obtained solution was refluxed under heating for 24 hours. After the solvent was distilled away from the solution, a semisolid residue thus obtained was washed several times with methyl-t-butyl ether, under an argon flow, to remove excess of the alkylating agent and the unreacted deprotonated dye, until the filtrate was nearly colorless. A solid residue was separated therefore, which is silanized BB7. Then, 1 g of the silanized BB7 was dissolved in 25 mL of anhydrous ethanol to obtain a silanized BB7 solution.

First, 25 mL of the silanized BB7 solution was added to a mixed solvent of 150 mL of ethanol (96%), 50 mL of water and 30 g of 25% ammonia aqueous solution and agitated vigorously at room temperature for 24 hours to form seed particles. Then, the mixture was subjected to centrifugation. A residue thus obtained was dispersed in ethanol (80%) and subjected to three cycles of washing and centrifugation. Thereafter, the solvent was removed therefrom to obtain a residue. The thus-obtained residue was dispersed in dimethyl sulfoxide (DMSO), added in 400 mL of deionized water and agitated. Furthermore, a 12-molybdo phosphoric acid n-hydrate was added thereto, thereby color material S of Comparative example 10 was obtained.

[Evaluation Methods]

(Evaluation of Solubility)

First, 0.05 g of each of color materials A to S of Examples 1 to 9 and Comparative examples 1 to 10, was put in a sample tube, and methanol (manufactured by: KANTO CHEMICAL CO., INC.) was added thereto so that the total weight (excluding the sample tube) was 1.0 g. A magnetic stirrer was put in the sample tube to agitate the mixture for 1 hour at room temperature. Then, a visual inspection was performed to observe whether the color material was dissolved or not. In Table 1, "○" means that the color material was dissolved, and "x" means that the insoluble substance was found.

(Measurement of Decomposition Point)

About 5 mg of each of color materials A to S of Examples 1 to 9 and Comparative examples 1 to 10, was put in a quartz pan, and measured by means of a differential thermogravimetric analyzer (TG-DTA) (product name; TG8120; manufactured by: Rigaku Corporation) up to 800° C. at a heating rate of 10° C./minute, placing alumina on the quartz pan as a reference. The extrapolation temperature of the peak of the thus-obtained TG curve was used as the decomposition point. The temperature of the decomposition point can be used as an indicator of heat resistance.

(Measurement of Thermal Stability)

About 5 mg of each of color materials A to S of Examples 1 to 9 and Comparative examples 1 to 10, was put in a quartz pan and heated up to 230° C. at a heating rate of 10° C./minute, placing alumina on the quartz pan as a reference, by means of a differential thermogravimetric analyzer (TG-DTA) (product name; TG8120; manufactured by: Rigaku Corporation). After reaching 230° C., the temperature was kept for 60 minutes at 230° C. Then, a weight reduction rate was measured. The weight reduction rate was calculated by the following formula and can be used as an indicator of heat resistance.

Weight reduction rate=(weight before heating−weight after heating)/weight before heating×100(%)

The measurement results are shown in Table 1.

TABLE 1

| | Color material | a | c | Solubility in methanol | Decomposition point (° C.) | Weight reduction rate |
|---|---|---|---|---|---|---|
| Example 1 | A | 2 | 2 | x | 253 | −19.1 |
| Example 2 | B | 2 | 3 | x | 258 | −10.7 |
| Example 3 | C | 2 | 3 | x | 262 | −6.7 |
| Example 4 | D | 2 | 2 | x | 268 | −7.2 |
| Example 5 | E | 2 | 4 | x | 270 | −6.9 |
| Example 6 | F | 2 | 300 | x | 272 | −6.3 |
| Example 7 | G | 2 | 3 + 300 | x | 267 | −5.5 |
| Example 8 | H | 2 | 3 | x | 288 | −4.6 |
| Example 9 | I | 2 | 4 | x | 292 | −5.2 |
| Comparative example 1 | J | 2 | 1 | ○ | 248 | −35.1 |
| Comparative example 2 | K | 1 | 2 | ○ | 237 | −32.8 |
| Comparative example 3 | L | 1 | 3 | ○ | 241 | −31.8 |
| Comparative example 4 | M | 1 | 2 | ○ | 250 | −32.2 |
| Comparative example 5 | N | 1 | 4 | ○ | 251 | −38.3 |
| Comparative example 6 | O | 1 | 300 | ○ | 246 | −36.2 |
| Comparative example 7 | P | 1 | 3 + 300 | ○ | 248 | −34.5 |
| Comparative example 8 | Q | 1 | 3 | ○ | 258 | −30.1 |
| Comparative example 9 | R | 1 | 4 | ○ | 259 | −30.5 |
| Comparative example 10 | S | ≥1 | 3 | x | 242 | −28.5 |

From the measurement results shown in Table 1, the following are understood.

Each of color materials A to I of Examples, in which molecular associations were formed by the combination of divalent or trivalent anions and the color material precursor comprising divalent cations, had a higher thermal decomposition temperature and showed a lower weight reduction rate after heated at 230° C. for 1 hour, compared with those of Comparative examples 1 to 10. From these facts, it is clear that each of color materials A to I of Examples 1 to 9 had higher heat resistance. The reason is assumed as follows: in color materials A to I of Examples 1 to 9, each comprising counter cations and counter anions, formation of consecutive ion pair association as shown in FIG. 1 exerted an effect to increase the apparent molecular weight; moreover, due to an increase in the cohesion in a solid state, there was a decrease in the heat-induced motion of the ions and resulted in prevention of dissociation or decomposition of the ion pairs. This can be also understood from the fact that color materials A to I of Examples 1 to 9 had significantly lower solubility in methanol than those of Comparative examples 1 to 9.

For color material S of Comparative example 10, insoluble substances were observed in methanol; however, it is apparent from the color of the methanol that the solubility of color material S was higher than those of Examples 1 to 9. The reason is assumed that the unreacted dye (BB7) remaining in color material S and the color material having low polymerization degree were dissolved in methanol. In addition, color material S had lower heat resistance compared with color materials A to I of Examples 1 to 9. Color material S included highly-polymerized, high-molecular-weight components derived from the polysiloxane dye cations and the remaining unreacted dye cations, so that color material S had molecular weight distribution derived from the cationic moieties. Particularly, it is assumed that since the unreacted dye cations are monovalent cations, the cations formed terminal positions of the molecular associations and resulted in the insufficient apparent molecular weight of the molecular associations. From the above reasons, color material S is assumed to have low heat resistance.

<Evaluation: Insolubility in Solvent>

First, 0.1 g of each of color materials A to I of Examples 1 to 9 was put in 10 g of PGMEA in a 20 mL sample tube. The sample tube was covered with a lid, shaken well for 20 seconds and then left for 10 minutes. Then, 5 g of the supernatant was filtered to remove insoluble substances. The thus-obtained filtrate was measured for absorption spectrum, using a cm cell in an ultraviolet and visible spectrophotometer (product name: UV-2500PC; manufactured by: SHIMADZU CORPORATION) to calculate the absorbance (595 nm) at the wavelength of 595 nm.

If the absorbance (595 nm) measured under the above condition is 2 or less, it can be said that PGMEA is a solvent which does not substantially dissolve color material. The results are as shown in Table 2.

○: absorbance (595 nm)≤2
x: absorbance (595 nm)>2

TABLE 2

| | Insolubility of color material | | |
|---|---|---|---|
| | Color material | Solvent | Insolubility |
| Example 1 | A | PGMEA | ○ |
| Example 2 | B | PGMEA | ○ |
| Example 3 | C | PGMEA | ○ |
| Example 4 | D | PGMEA | ○ |
| Example 5 | E | PGMEA | ○ |
| Example 6 | F | PGMEA | ○ |
| Example 7 | G | PGMEA | ○ |
| Example 8 | H | PGMEA | ○ |
| Example 9 | I | PGMEA | ○ |

Color materials A to I of Examples 1 to 9 were not substantially dissolved in PGMEA. From the above results, it can be said that PGMEA is a solvent which does not substantially dissolve color materials A to I of Examples 1 to 9.

Color materials A to I of Examples 1 to 9 were dispersible in PGMEA. Therefore, the color material of the present invention can be dispersed in the solvent for use, which does not substantially dissolve the color material.

REFERENCE SIGNS LIST

1: Divalent or higher counter cation
2: Divalent or higher counter anion
3: Linkage by A
4: Ionic bond
5: Cation
6: Conventional dye salt-forming compound
10: Molecular association of color material of the present invention

The invention claimed is:

1. A color material represented by the following general formula (I):

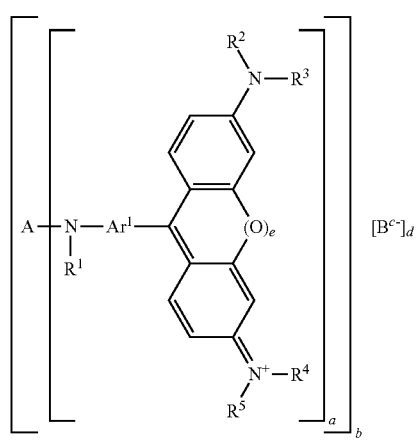

General formula (I)

wherein A is an "a"-valent organic group in which a carbon atom directly bound to N of the general formula (I) has no π bond, and the organic group is a cyclic aliphatic hydrocarbon group having a saturated aliphatic hydrocarbon group at least at a terminal position directly bound to the N of the general formula (I), or an aromatic group having a saturated aliphatic hydrocarbon group at least at a terminal position directly bound to the N of the general formula (I), and O, S, N may be contained in a carbon chain of the organic group; $B^{c-}$ is a "c"-valent organic anion having a sulfonato group (—$SO_3^-$ group) or a "c"-valent anion of an inorganic acid containing molybdenum and/or tungsten; each of $R^1$ to $R^5$ is independently a hydrogen atom, an alkyl group which may have a substituent, or an aryl group which may have a substituent; $R^2$ and $R^3$ may be bound to form a ring structure, and/or $R^4$ and $R^5$ may be bound to form a ring structure; $Ar^1$ is a divalent aromatic group which may have a substituent; $R^1$s may be the same or different; $R^2$s may be the same or different; $R^3$s may be the same or different; $R^4$s may be the same or different; $R^5$s may be the same or different; and $Ar^1$s may be the same or different; and wherein each of "a" and "c" is an integer of 2 or more; each of "b" and "d" is an integer of 1 or more; "e" is 0 or 1 and there is no bond when "e" is 0; and "e"s may be the same or different.

2. The color material according to claim 1, wherein the anion ($B^{c-}$) in the general formula (I) is one or more anions selected from the group consisting of those represented by the following general formulae (II), (III) and (IV):

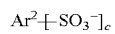

General formula (II)

wherein $Ar^2$ is a "c"-valent aromatic group which may have a substituent, and "c" is an integer of 2 or more;

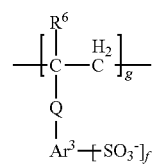

General formula (III)

wherein $R^6$ is a hydrogen atom or a methyl group; $Ar^3$ is an aromatic group which may have a substituent; Q is a direct bond or a divalent linking group; "f" is an integer of 1 or more; and "g" is an integer of 2 or more; and

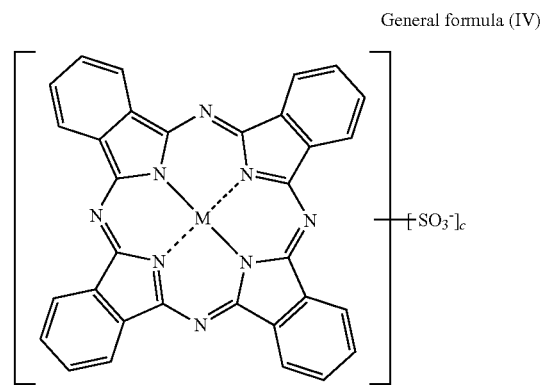

General formula (IV)

wherein M represents two hydrogen atoms or one selected from the group consisting of Cu, Mg, Al, Ni, Co, Fe and Zn; the sulfonato group (—$SO_3^-$ group) is bound to an aromatic ring by substitution; and "c" is an integer of 2 to 4.

3. The color material according to claim 1, wherein "a" in the general formula (I) is 4 or less.

4. A method for producing a color material represented by the following general formula (I) comprising the step of: performing a condensation reaction between a compound represented by the following general formula (A) and a compound represented by the following general formula (B):

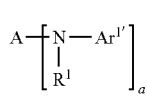

General formula (A)

General formula (B)

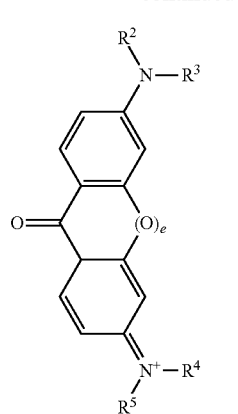

General formula (I)

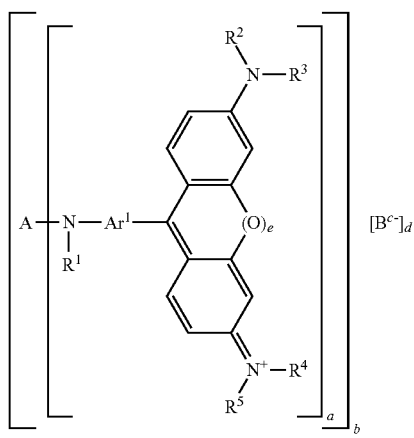

wherein A is an "a"-valent organic group in which a carbon atom directly bound to N of the general formula (I) has no π bond, and the organic group is a cyclic aliphatic hydrocarbon group having a saturated aliphatic hydrocarbon group at least at a terminal position directly bound to the N of the general formula (I), or an aromatic group having the aliphatic hydrocarbon group, and O, S, N may be contained in a carbon chain of the organic group; $B^{c-}$ is a "c"-valent organic anion having a sulfonato group ($—SO_3^-$ group) or a "c"-valent anion of an inorganic acid containing molybdenum and/or tungsten; each of $R^1$ to $R^5$ is independently a hydrogen atom, an alkyl group which may have a substituent, or an aryl group which may have a substituent; $R^2$ and $R^3$ may be bound to form a ring structure, and/or $R^4$ and $R^5$ may be bound to form a ring structure; $Ar^1$ is a divalent aromatic group which may have a substituent; $Ar^1$ is a monovalent aromatic group in which a hydrogen atom is bound to $Ar^1$; $R^1$s may be the same or different; $R^4$s may be the same or different; $R^5$s may be the same or different; $R^4$s may be the same or different; $R^5$s may be the same or different; and $Ar^1$s may be the same or different; and wherein each of "a" and "c" is an integer of 2 or more; each of "b" and "d" is an integer of 1 or more; "e" is 0 or 1 and there is no bond when "e" is 0; and "e"s may be the same or different.

* * * * *